(12) United States Patent
Schultz et al.

(10) Patent No.: US 10,227,252 B2
(45) Date of Patent: Mar. 12, 2019

(54) METHOD AND APPARATUS FOR PRODUCING A TUBE PARTIALLY HAVING A NON-CIRCULAR CROSS SECTION AND HAVING CIRCULAR END PORTIONS AND USE THEREOF

(71) Applicant: Schott AG, Mainz (DE)

(72) Inventors: Nikolaus Schultz, Essenheim (DE); Nikolaos Katsikis, Waldsassen (DE); Volker Trinks, Mitterteich (DE); Reinhard Maennl, Mitterteich (DE)

(73) Assignee: SCHOTT AG, Mainz (DE)

( * ) Notice: Subject to any disclaimer, the term of this patent is extended or adjusted under 35 U.S.C. 154(b) by 652 days.

(21) Appl. No.: 14/470,970

(22) Filed: Aug. 28, 2014

(65) Prior Publication Data
US 2015/0064779 A1    Mar. 5, 2015

(30) Foreign Application Priority Data
Aug. 30, 2013 (DE) ........................ 10 2013 109 454

(51) Int. Cl.
*C12M 3/00* (2006.01)
*C03B 23/049* (2006.01)
(Continued)

(52) U.S. Cl.
CPC .......... *C03B 23/049* (2013.01); *B29C 53/086* (2013.01); *C03B 23/045* (2013.01);
(Continued)

(58) Field of Classification Search
CPC ................................................. C03B 23/049
See application file for complete search history.

(56) References Cited

U.S. PATENT DOCUMENTS

| | | | |
|---|---|---|---|
| 4,050,601 A | 9/1977 | Bogaard | |
| 4,142,514 A | 3/1979 | Newton | |

(Continued)

FOREIGN PATENT DOCUMENTS

| | | |
|---|---|---|
| DE | 545449 C | 2/1932 |
| DE | 1007962 B | 5/1957 |

(Continued)

OTHER PUBLICATIONS

English language machine translation of JP2006004880, pp. 1-10 (accessed Mar. 28, 2018). (Year: 2018).*

(Continued)

*Primary Examiner* — William H. Beisner
(74) *Attorney, Agent, or Firm* — Ohlandt, Greeley, Ruggiero & Perle, L.L.P.

(57) ABSTRACT

Disclosed is a method for the production of a tube having, in sections, a non-circular profile by deforming, comprising:
  a) providing a tube, which has a circular initial profile;
  b) conveying the tube in a hot, malleable state through a nip, which is formed by squeezing rollers and has a first nip width, which is larger than or equal to an outer dimension of the initial profile;
  c) adjusting the squeezing rollers for setting a second nip width, which is smaller than the outer dimension of the initial profile, and deforming the initial profile in said hot, malleable state for obtaining said non-circular cross section; and
  d) adjusting the squeezing rollers for setting a third nip width, which is larger than or equal to the outer dimension of the initial profile, and severing said tube in a region having a circular cross section;
so that respective end portions of said tube have a circular cross section
According to the invention, the tubes can be connected reliably with connecting-members or other tubes via the end
(Continued)

portions having the circular profile using proven tube connection technologies. At the same time there is at least one central section having a non-circular cross section which is of advantage, for example for applications in photobioreactors.

14 Claims, 17 Drawing Sheets

(51) Int. Cl.
| | |
|---|---|
| *C03B 23/055* | (2006.01) |
| *B29C 53/08* | (2006.01) |
| *C03B 23/045* | (2006.01) |
| *C12M 1/00* | (2006.01) |
| *C12M 1/12* | (2006.01) |
| *G01B 11/04* | (2006.01) |
| *G01B 11/08* | (2006.01) |
| *G01B 11/12* | (2006.01) |
| *C03B 23/09* | (2006.01) |
| *B29K 101/12* | (2006.01) |
| *B29K 105/00* | (2006.01) |

(52) U.S. Cl.
CPC ............ *C03B 23/055* (2013.01); *C12M 21/02* (2013.01); *C12M 23/06* (2013.01); *C12M 23/22* (2013.01); *G01B 11/043* (2013.01); *G01B 11/08* (2013.01); *G01B 11/12* (2013.01); *B29K 2101/12* (2013.01); *B29K 2105/258* (2013.01); *C03B 23/095* (2013.01)

(56) References Cited

U.S. PATENT DOCUMENTS

| | | | |
|---|---|---|---|
| 2003/0116251 | A1 | 6/2003 | Almann |
| 2010/0309393 | A1* | 12/2010 | Yoshikawa ....... G02F 1/133604 348/790 |
| 2011/0235320 | A1* | 9/2011 | Cai ....................... F21V 19/045 362/217.17 |

FOREIGN PATENT DOCUMENTS

| | | |
|---|---|---|
| DE | 10014653 | 10/2001 |
| DE | 102006015223 B3 | 8/2007 |
| DE | 102009000154 | 7/2010 |
| DE | 10 2010 043 587 A1 | 5/2012 |
| JP | 61224257 A | 10/1986 |
| JP | H06114910 | 4/1994 |
| JP | 2006-4660 A | 1/2006 |
| JP | 2006004880 A * | 1/2006 |
| JP | 2006-315919 A | 11/2006 |
| WO | 2009051479 A2 | 4/2009 |

OTHER PUBLICATIONS

Product brochure of Applicant Schott, Algae Brochure Row, Aug. 2012, webfinal, 20 pp.

Search Report of the European Patent Office dated Jan. 15, 2015 for corresponding European Patent Application No. 14181847.6, 5 pages.

* cited by examiner

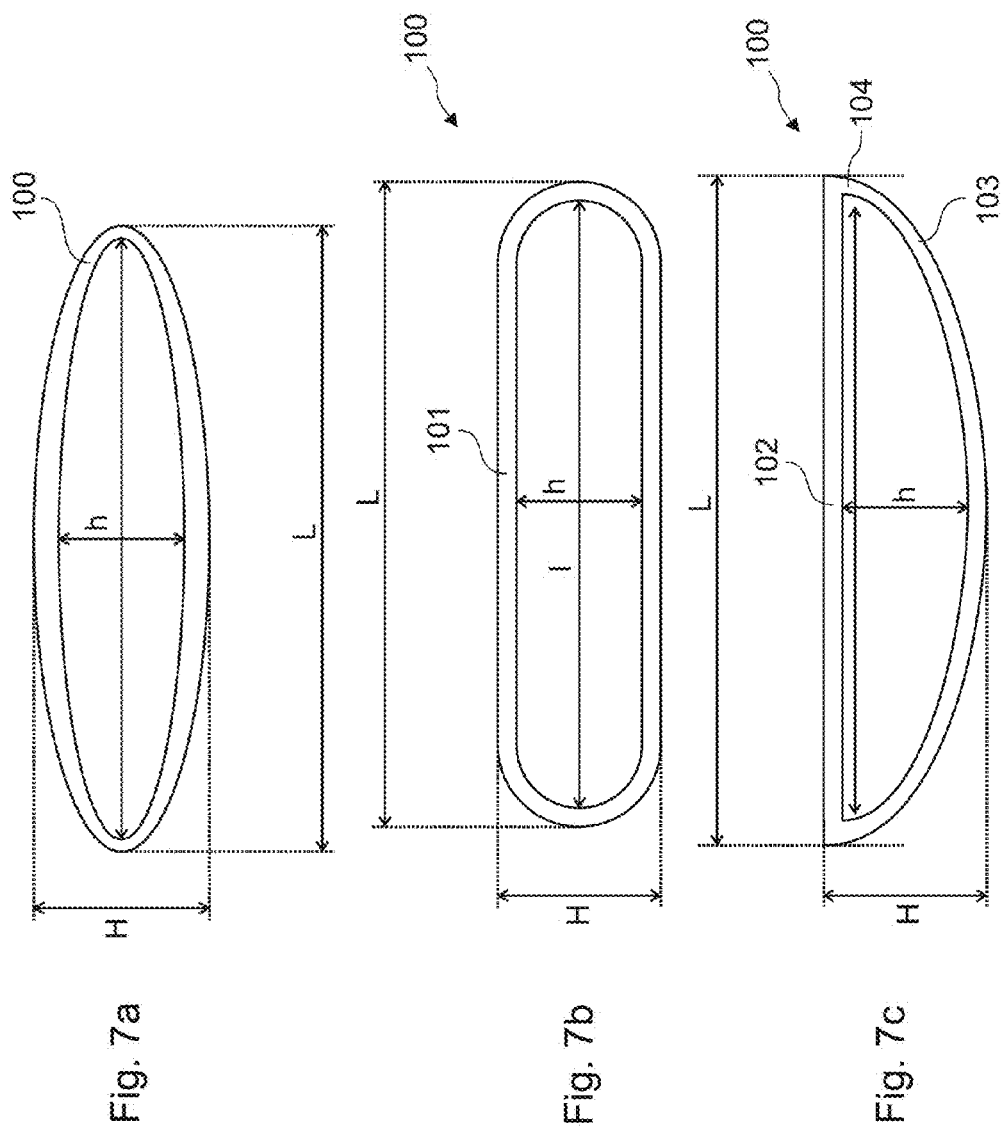

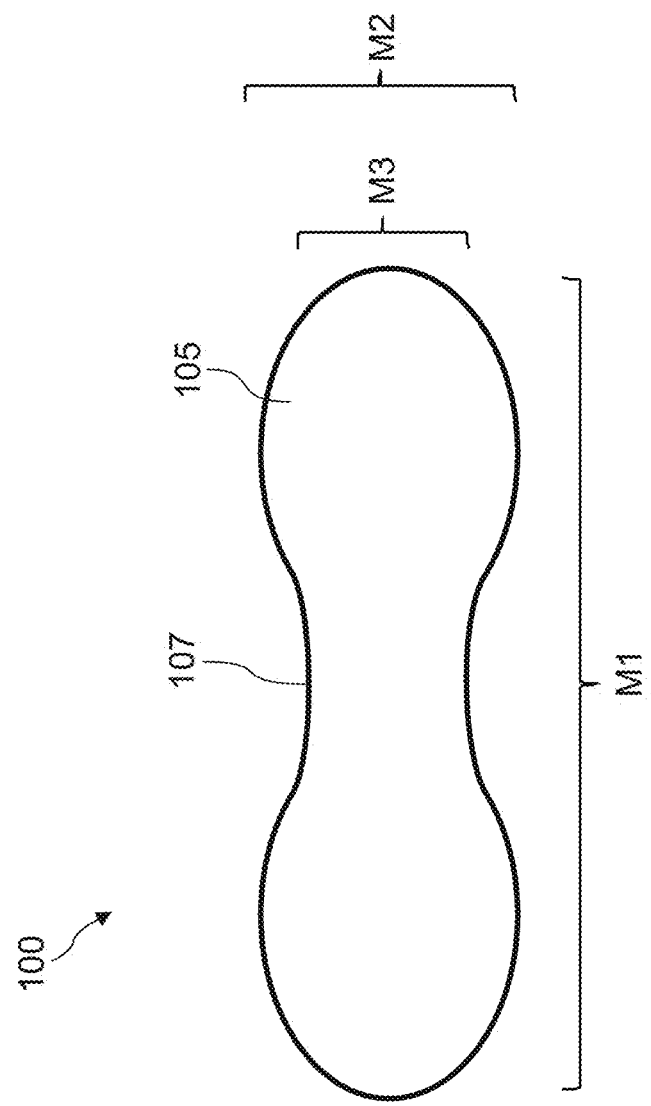

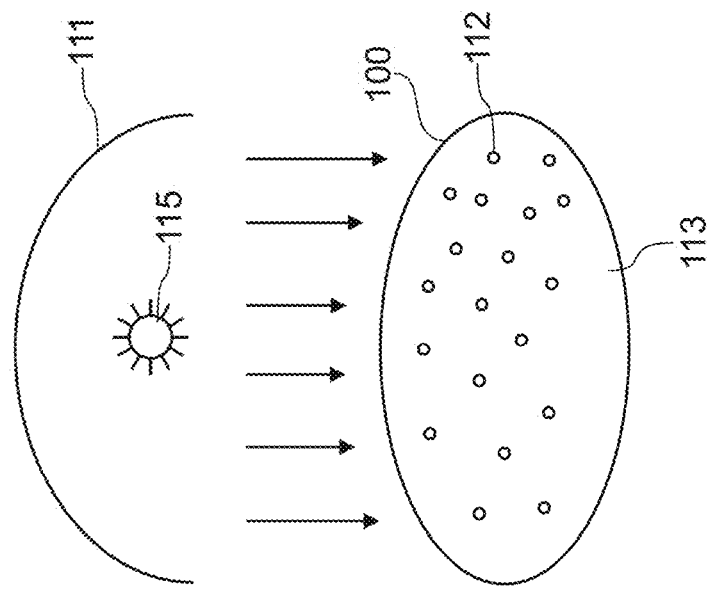
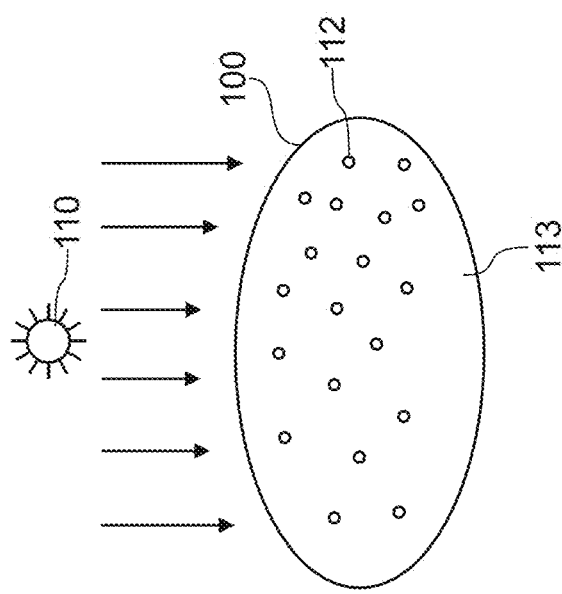

METHOD AND APPARATUS FOR PRODUCING A TUBE PARTIALLY HAVING A NON-CIRCULAR CROSS SECTION AND HAVING CIRCULAR END PORTIONS AND USE THEREOF

The present application claims the priority of German Patent Application No. 10 2013 109 454.6, "Method and apparatus for producing a tube partially having a non-circular cross section and having circular end portions. Use thereof and Tube", filed on 30 Aug. 2013, the whole content of which is hereby incorporated by way of reference.

FIELD OF THE INVENTION

The present invention generally relates to the production of tubes having a profile, which is different to a circular shape, with high precision, for example for use as an oval tube, and relates more specifically to the production of tubes having a non-circular cross section in sections and having circular end portions, in particular made of a transparent glass or plastic material. Further aspects of the present invention relate to an apparatus for the production of such tubes, to preferred uses thereof and to tubes having a profile as described in the following.

BACKGROUND OF THE INVENTION

Conventionally tubes have a constant cross section over their entire length. From the prior art e.g. glass tubes having a circular cross section are known for use as packaging containers for pharmaceutical substances, for use in lighting or for applications in solar heating. Oval glass tubes having a non-circular cross section are distributed by the applicant under the trademarks Conturax® und Conturax Pro®. Their profile is constant over the entire length of the glass tubes. Oval tabes are also used for fluorescent lamps (see JP 61224257 A2).

Tubes of plastic material or of a plastic composite material having a non-circular cross section are used e.g. in floor heating systems.

DE 545 449 A discloses an apparatus for deforming or shaping glass tubes to glass tubes having a non-circular profile, wherein the glass tubes are conveyed through a nip in a heated state. DE 1007962 A discloses a corresponding method for shaping glass tubes to thin insulating tapes or insulating layers. DE 102006015223 B3 of the Applicant discloses a method and an apparatus for producing a glass tube having a profile that differs from a circular profile. Here, the initial glass tube having the initial profile (so-called preform) first passes through a hot zone while forming a drawing bulb and then passes a nip formed by a pair of rollers, where the drawing bulb is shaped (deformed) to a glass tube having a different profile. All of the aforementioned glass tubes have a constant profile over their entire length.

JP 2006315919 A und JP 2006004660 A2 disclose glass tubes for cold-cathode fluorescent lamps (CCFL) having sections that have a non-circular cross section, that alternate with sections that have a circular cross section. For this purpose, a glass tube is deformed, in sections, in a hot malleable state and is partially also bent. The glass tubes are molten off at the ends, but are not open at their ends and thus cannot be connected with connecting members or adjacent glass tubes.

SUMMARY OF THE INVENTION

It is an object of the present invention to provide a method and an apparatus for the production of tubes, in particular of glass tubes, having, in sections, a non-circular cross section that can be connected in a more convenient and reliable manner with connecting members or adjacent tabes. According to a further aspect of the present invention preferred uses of such tubes, particularly of such glass tubes, shall also be provided.

According to the present invention there is provided a method for the production of a tube having, in sections, a non-circular profile by deforming, comprising the steps of: a) providing a tube, which has a circular initial profile (a circular initial cross section); b) conveying tire-tube in a hot malleable state, through a nip, which is formed by squeezing rollers and has a first nip width which is larger than or equal to an outer dimension of the initial profile; c) adjusting the squeezing rollers for setting a second nip width, which is smaller than the outer dimension of the initial profile, and deforming the initial profile in said hot, malleable state for obtaining said non-circular cross section; and d) adjusting the squeezing rollers for setting a third nip width, which is larger than or equal to the outer dimension of the initial profile, and severing said tube in a portion having a circular cross section; so that respective end portions of said tube have a circular cross section. In the sense of the present application the term "circular cross section" shall mean that the cross section (profile) has an exactly circular cross section, which deviates from a perfect circular cross section only within the limits of standard production tolerances.

Because of the plastic deformation in step c) the tube, which is conveyed through the nip in a malleable state, is deformed to the desired non-circular cross section, e.g. to obtain an oval or elliptic tube having a major axis and minor axis perpendicular thereto. Here, the length of the minor axis or the minimum outer dimension of the tube after the deformation may be adjusted precisely by the width of the nip through which the tube is conveyed. This non-circular cross section may extend with a constant cross section over an extended distance, e.g. in a central section of the tube, but may also vary.

Because the tube, which is conveyed into the nip and has a circular cross section, is not deformed in steps b) and d), because the width of the nip is larger than or equal to a maximum outer dimension of the input tube, the tube has a circular-shaped or perfect circular cross section at both end portions. Thus various tube connecting technologies are available for connecting with connecting members or with adjacent tubes, which also have end portions having a circular profile, said connecting technologies enabling a precise and reliable connection in a simple manner. For this purpose it is only necessary that the tubes are only severed at the end portions having the circular cross section, but not in those regions, which have a non-circular cross section. This holds in particular for the use of glass tubes for solar heating or in photo-bioreactors.

For the purpose of forming tubes having a circular cross section and of deforming such tubes to tubes having a non-circular cross section with high precision and at low costs well-established methods and apparatuses are known from the prior art. Here, the tube may be drawn through the nip by means of a drawing device. In addition or as an alternative to the drawing device the squeezing rollers, which form the nip, may also be actively driven in order to drive the tube exclusively or additionally.

According to a further embodiment the deformation is performed such that a circumferential length of said non-circular profile and the circumferential length of said end portions of said tube having a circular cross section are equal to each other.

According to a further embodiment a conveying length of the tube (a distance over which the tube is conveyed) is measured, wherein an axial length of a section having said non-circular cross section and/or an axial length of transition portions between the end portions of die tube and said non-circular profile is/are adjusted on the basis of a value for the respective conveying length. Thus, the cross sections or profiles of such transition portions and their variation in axial direction can be adjusted precisely, wherein the value for the conveying length serves as a reliable reference value.

According to a further embodiment, for this purpose the adjusting of the squeezing rollers in steps c) and d) is performed according to a predetermined adjustment function for forming the transition portions between the end portions of the tube and said non-circular profile such that these transition portions have a cross section in accordance with the predetermined adjustment function. For this purpose the width of the nip may be adjusted according to a linear function. In general, however, for this purpose also non-linear functions may be used, wherein continuous functions are preferred.

According to a further embodiment the deforming of the initial profile to said non-circular profile in step c) is performed in a hot, malleable state. This holds in particular for the deforming of tubes made of glass at high temperatures above the softening point of the respective glass or also for the deforming of tubes made of plastic material at suitable temperatures. The width of the nip is thereby accurately predetermined and maintained during the deforming process, in order to achieve the desired accuracy along the minor axis of the tube. Fluctuations before the shaping process, which are caused by the amount of glass or plastic material fed and by other effects, are "transferred" to the large (un-squeezed) outer diameter of the glass tube or plastic tube (which is often not so important). Thus, the dimensions can be very accurately predetermined in the direction of extension of the nip.

According to a further embodiment the position of at least one of the squeezing rollers is continuously varied so that a contact area between the respective squeezing roller and the hot tube body is continuously varied or changed. By this surprisingly simple measure according to the present invention particularly glass tubes having, in sections, a non-circular profile can be produced with even higher precision, because according to the present invention the area of contact between the hot glass and the squeezing rollers varies continuously. As a result, various problems can be prevented in comparison to conventional squeezing units operated with a (quasi-) stationary position of the squeezing rollers. Quasi-stationary in this context means especially that the position of contact between the squeezing rollers and the hot material to be deformed is not varied. Damages or scratches in the surface of the material to be deformed caused by overheated squeezing rollers, small particles or the like can thus be torn from the surface of the body during squeezing or deformation and thus do not affect the further shaping or deformation process. Different temperatures on the surface of the squeezing rollers that conventionally result in different widths of the nip and thus result in poor tolerances due to the variation of the contact area, can be also reduced. Furthermore, an undesirable overheating of the contact surface between the body and the squeezing rollers can be prevented, which conventionally had often resulted in clearly visible undesirable "heat tracks" on the outer surface of the body. The squeezing rollers may also be used in the method of this embodiment over a longer period. Particularly, according to this embodiment a mechanical polishing of the squeezing rollers before their reuse, if at all required, in any event is necessary less often. By means of the method according to the present invention also a smoother and more constant outer surface of the body can be achieved.

Due to their continuous adjustment in general the squeezing rollers can be operated without cooling, which often caused additional problems in a conventional method concerning the dimensional accuracy of the squeezed body.

Preferably, the nip is formed by two opposite squeezing rollers which are each mounted displaceable and extending in parallel with each other. Although in general it may be sufficient if the position of only one of these two squeezing rollers is adjusted continuously (in axial direction), according to a further embodiment preferably the positions of both squeezing rollers are continuously adjusted (in axial direction). Preferably, both squeezing rollers are axially adjusted together and in synchronism with each other.

In order to achieve the aforementioned continuous adjustment of the respective squeezing roller, an adjusting device or drive is associated with the respective squeezing roller, which is coupled to the respective squeezing roller and adjusts it such that a contact area between the respective squeezing roller and the hot body is continuously varied or changed.

According to a further embodiment the aforementioned continuous adjustment of the respective squeezing roller may be performed while maintaining the actual nip width between the squeezing rollers that form the nip. This does not exclude that, in addition, also the width of the nip between the squeezing rollers that form this nip is controlled or regulated, for example in order to achieve a constant outer dimension of the body or a constant wall thickness thereof. The adjustment of the respective squeezing roller and such a control or regulation of the width of the nip, however, are preferably not coupled to each other and are performed for a completely different purpose. This can for example also result in considerably different time scales involved in the continuous adjustment of the position(s) of the respective squeezing roller(s) and in the controlling or regulation of the width of the nip.

According to a further embodiment, the position of said at least one squeezing roller and preferably of the two squeezing rollers is varied by means of a continuous axial adjustment of the squeezing rollers in accordance with a predetermined adjustment function. Suitably, this adjustment function is carried out mainly steadily and can for example be carried out according to a sawtooth or sinusoidal signal, for which purpose it should be ensured that a too-long persistence of the squeezing roller(s) at the same position is avoided, because otherwise the disadvantages of the conventional shaping process would occur again.

According to a preferred further embodiment, the adjustment function is performed as a cyclic reciprocating displacement of the respective squeezing roller or preferably of both squeezing rollers forming the nip in the axial direction thereof. Preferably, this reciprocating displacement is symmetric in time.

According to a further embodiment, the adjustment function is performed in discrete steps of the same step size, which favors the implementation of the adjustment function using standard synchronous motors or stepper motors or the like.

According to a further embodiment, a rotational movement of the squeezing rollers forming the nip is driven separately. This enables an adjustment of the profile of the body with high-precision after the shaping process, for example a precise adjustment of the oval shape of an oval tube to be produced in portions that are not the end portions of the tube. Preferably, the squeezing rollers are driven in synchronism with the speed at which the body is passed through the nip.

According to a further embodiment the rotational movement of the squeezing rollers forming the nip is driven in synchronism or with a predetermined constant offset, so that it is possible to vary the drawing speed at which the body is drawn through the nip and at the same time to vary the speed of the squeezing rollers automatically.

According to a further embodiment, an outer dimension and/or internal dimension of said different profile of the body is detected downstream of the nip and a parameter relevant for the shaping of the hot, malleable body to a body having said different profile is controlled or regulated according to the detected outer dimension and/or internal dimension of said different profile to maintain the outer dimension and/or internal dimension of said different profile constant.

For this purpose, for example, the outer diameter and/or the inner diameter may be measured and monitored continuously by means of an optical measuring method, which is performed downstream of the nip and is suitably performed upstream of a drawing device which draws the body through the nip. In the case of an undesired fluctuation the relevant parameter can then be readjusted or regulated in order to achieve an even higher precision.

According to a further embodiment, the squeezing rollers that form the nip are automatically measured, in particular their true-running characteristics and/or their outer diameter, and these squeezing rollers are then positioned relative to each other by means of a regulating means such that the true-running errors and/or fluctuations of the outer diameter, based on the nip width, are minimum.

According to a further embodiment this parameter may be the width of the nip, a respective rotational speed or differential rotational speed of the squeezing rollers forming the nip or an over-pressure to be applied to an inner volume of the malleable body embodied as a glass tube.

According to a further embodiment the body is marked and/or sorted out according to the outer dimension and/or internal, dimension detected downstream of the nip. Thus batches having predetermined tolerances can be produced easily.

In order to accomplish the aforementioned adjustment of the squeezing rollers, at least one adjusting device is associated with the squeezing rollers, and preferably with each of the squeezing rollers. According to a preferred embodiment, the adjusting device comprises a translation stage and an adjusting motor for adjusting said translation stage, wherein the squeezing rollers are supported on the translation stage, wherein the translation stage is mounted so as to be displaceable in axial direction of the squeezing rollers and wherein the adjusting motor is coupled to the translation stage to effect said axial adjustment of the at least one squeezing roller by adjusting the translation stage.

According to a further embodiment, the axes of the squeezing rollers, which form the nip converge in a V-shaped manner, which enables a larger variability during the forming of the profile (cross section) of the tube between the end portions having the circular cross section. Particularly, tubes having drop-shaped central sections can be achieved by means of a V-shaped convergence of the squeezing rollers.

According to a further embodiment, the squeezing rollers, which form the nip, have a non-circular profile, in particular an oval or polygonal profile, so that the profile of the tube between the end portions having a circular profile may be varied, if viewed in axial direction, e.g. so that the profile has undulations or bulgings and projections. In this manner particularly regular contours may be formed on the outer circumference of the central section between the end portions having a circular cross section.

According to a further embodiment, the squeezing rollers, which form the nip, have a rotationally symmetric profile and a contour, which deviates from a linear shape, i.e. a contour, which is different to a cylindric shape if viewed in axial direction. Thus, according to the present invention an even larger variability between the end portions having the circular cross section may be accomplished when forming the profile of the tube.

According to a further embodiment, the squeezing rollers form a mirror-symmetric nip, wherein the contour of the respective squeezing roller comprises at least one recess or at least one projection. In this manner tubes having central sections of a virtually arbitrary profile between the end portions having a circular cross section may be formed, e.g. recesses. Such tubes particularly may maintain a certain degree of symmetry in their central sections, e.g. may be formed in an axial-symmetric or mirror-symmetric manner.

According to a further embodiment, the squeezing rollers, which form the nip, are actively driven. Thus it can e.g. be prevented that the tube material jams before the nip in the malleable state during the deforming process, e.g. if tubes shall be produced that have a central section of a high ovality between the end portions having the circular cross section. According to a further embodiment, such an active drive of the squeezing rollers may even replace a drawing device, which is usually provided for drawing the tube from an upstream production plant and/or through the nip, e.g. during the production of glass tubes. The active drive of the squeezing rollers forming the nip may be controlled or regulated in a suitable manner in order to implement constant conditions and forces in the region of the nip. Particularly, the active drive of the squeezing rollers forming the nip may result in a reduced strain of the tube material during the conveyance through the nip, particularly in reduced material stress during cooling the tube downstream of the nip, and may in particular also prevent a rupture of the tube material, which conventionally is always likely to occur, if the tube material is drawn through the nip with excessive forces, e.g. during the production of glass tubes.

According to a further embodiment, the squeezing rollers, which form the nip, are additionally heated. This may ease a deformation of the tube material during the conveyance through the nip, because the tube material is selectively heated locally or because the temperature of the tube material is suitably set in order to enable a suitable plasticity in this region. Particularly the pressure exerted on the tube material in the nip may be reduced further, which enables the production of tubes having even less strain. A heating of the squeezing rollers, which form the nip, may also enable a larger variability in the design of the production plant and tighter tolerances. Namely, while conventionally the squeezing rollers need to be positioned at regions where the tube material to be cooled is still in a suitable malleable state, according to the invention the squeezing rollers may also be positioned at a different position, in particular downstream of the conventional position, because the tube material may again be put into a suitable malleable state due to the heating of the squeezing rollers.

Particularly, such a heating is of advantage, if the squeezing rollers have a non-circular profile, because thus a sudden jamming of the tube material in the nip in case of a local variation of the profile of the nip may be prevented by a suitable adjustment of the temperature in the nip, particularly also by a time-dependent variation of said temperature.

According to a further embodiment, the squeezing rollers are adjusted in axial direction and/or the angle of incidence of the squeezing rollers is adjusted. Thus, according to the invention an even larger variability may be accomplished between the end portions having a circular profile during the forming of the profile of the tube.

A further aspect of the present invention relates to a corresponding apparatus for the production of a tube having, in sections, a non-circular profile (cross section) by deforming.

According to a further embodiment, such an apparatus may further comprise a measuring device for measuring a conveying length of the tube (a distance over which the tube is conveyed), wherein a controlling device additionally controls the adjusting device on the basis of a value for the respective conveying length of the tube such that an axial length of a section having said non-circular cross section and/or an axial length of transition portions between the end portions of the tube and said non-circular profile is/are adjusted on the basis of a value for the respective conveying length.

Tubes produced according to the above method, in particular tubes of a transparent glass or transparent plastic material, are particularly suited for all applications where tubes having a profile different from the ideal, circular profile are required or where such tubes at least offer advantages, but are to be connected with connecting members or coupling members, such as tube-shaped inlets or outlets, or with adjacent tubes.

According to the present invention a preferred first use relates to the use of a transparent tube for illuminating micro-organisms using an artificial light source or sun-light, in particular in a photobioreactor, wherein the tube comprises at least one central section having a non-circular cross section (profile) and two end portions respectively having a circular cross section (profile), wherein the tube is connected with an inlet and outlet or with adjacent tubes via the end portions and wherein the micro-organisms to be illuminated are positioned in an interior volume of the tube, in which use said at least one central section of the tube is positioned such that a broader side of said at least one section faces the artificial light source or the sun light or the direction of sun-light. Because of the smaller dimension of the tube in the direction of incidence of the illuminating radiation, e.g. of light, micro-organisms disposed inside the tube may be illuminated at higher intensity and more efficiently, which enables significant costs advantages when using the tubes produced according to the present invention.

According to the present invention a preferred second use relates to the use of a transparent tube for heating a fluid using sun-light, wherein the tube composes at least one central section having a non-circular cross section (profile) and two end portions respectively having a circular cross section (profile), wherein the tube is connected via the end portions with an inlet and outlet or with adjacent tubes and wherein a fluid to be heated, such as an oil absorbing sun-light, flows through an interior volume of the tube, in which use said at least one central section of the tube is positioned such that a broader side of said at least one section faces the sun light or the direction of sun-light. Because of the smaller dimension of the tube in the direction of incidence of the sun-light, the fluid flowing through the tube may be illuminated at higher intensity and more efficiently, which enables significant costs advantages when using the tubes produced according to the present invention.

A further aspect of the present invention relates to a photobioreactor for cultivating phototropic organisms, in particular (micro) algae, by light illumination, comprising at least one tube which accommodates a mixture of a liquid and the phototropic organisms, wherein said tube is transparent for the light, wherein said at least one tube comprises at least one central section having a non-circular cross section (profile) and two end portions respectively having a circular cross section (profile), wherein said tube is connected with an inlet and outlet or with an adjacent tube via said end portions and by means of connecting (coupling) members and wherein said at least one central section of the tube is positioned such that a broader side thereof faces the sun light or an artificial light source. Here, the tube is produced and formed as disclosed in the present application.

A further aspect of the present invention is directed to a tube, in particular to a tube made of a transparent material, preferably to a glass tube, comprising at least one central section having a non-circular-cross section (profile) and two end portions respectively having a circular cross section (profile), wherein the tube is made of a material, which is malleable in a heated state. Further preferred profiles of such tubes are described hereinafter in more detail.

OVERVIEW ON DRAWINGS

The invention will now be described by way of example and with reference to the accompanying drawings, from which further features, advantages and problems to be solved will be apparent. In the drawings:

FIGS. 7a-7e are examples of glass tubes, which are formed by means of an apparatus according to the present invention by means of a shaping process;

FIG. 9a shows the use of a tube according to the present, invention in a photobioreactor for cultivating micro-organisms by illumination according to a first embodiment;

FIG. 9b shows the use of a tube according to the present invention in a photobioreactor for cultivating micro-organisms by illumination according to a further embodiment;

FIG. 10b shows a squeezing roller for performing the method according to FIG. 10a;

In the drawings, identical reference numerals designate identical or substantially equivalent elements or groups of elements.

DETAILED DESCRIPTION OF PREFERRED EMBODIMENTS

Hereinafter the invention will be described with reference to an embodiment for deforming (shaping) glass tubes. However, the present invention is not limited to the deforming of glass tubes, but may be applied in the same manner also for tubes made of different materials, in particular for the deforming of tubes made of plastic materials or plastic composite materials.

Figure 1:
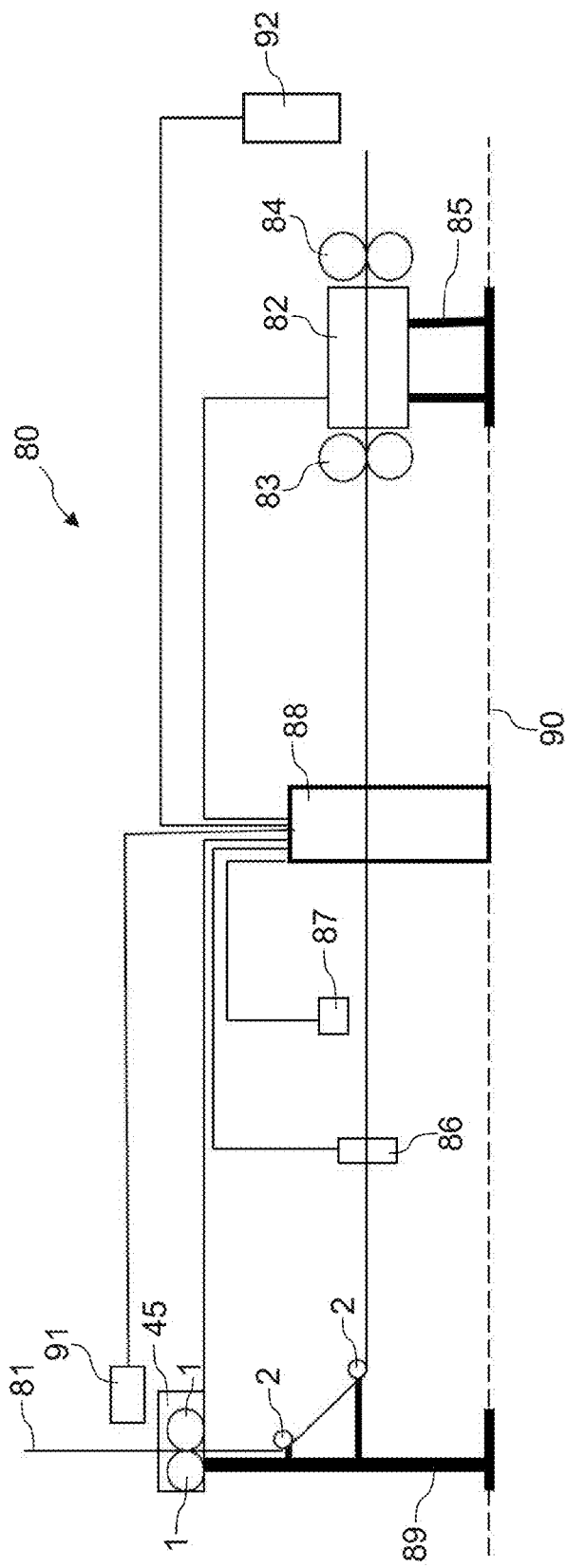
FIG. 1 shows a schematic view of a production plant for glass tubing according to the present invention.

According to FIG. 1, the apparatus generally designated by reference numeral 80 comprises a frame 89 on which two squeezing rollers 1 are mounted for shaping the glass tubing strand 81 entering the nip formed by these squeezing rollers 1 and on which two guide pulleys 2 are mounted downstream of the squeezing rollers 1 for deflecting the shaped glass tubing strand 81 towards the drawing device 82, which comprises two pairs of drawing rollers 83, 84. A cover 45, in which the squeezing rollers 1 are disposed, shields the region of shaping around the squeezing rollers 1 from the external environment.

The outer diameter of the glass tubing strand 81 is measured in a contact-less manner by means of a measurement device 86 preferably in a non-contact manner and most preferably optically. The inner diameter of the glass tubing strand 81 is measured optically by means of a measurement device 87, in particular using a triangulation method. The point of measurement of the measurement device 87 is preferably located as close to the point of measurement of the measurement device 86 as possible. Furthermore, characteristics of the two squeezing rollers 1 are measured or monitored automatically, for example by means of an inductive measurement method, e.g. for detecting the true-running errors and/or fluctuations of the outer diameter of the squeezing rollers. Furthermore, the conveying length of the tubing strand 81 (a distance over which the tubing strand 81 is conveyed) is measured by means of a measuring device 91, preferably without contacting the tubing strand 81.

As indicated by die connecting lines in FIG. 1, the relevant components of the plant 80 can be controlled or regulated by a controlling or regulating device 88, in particular by a CPU based on a software designed for this purpose. In this manner a control or regulation to a constant outer diameter of the glass tubes or to a constant wall thickness of the glass tube can be implemented or such that the true-running errors of the squeezing rollers 1, in relation to the width of the nip formed by the squeezing rollers 1, are minimum.

Figure 2:
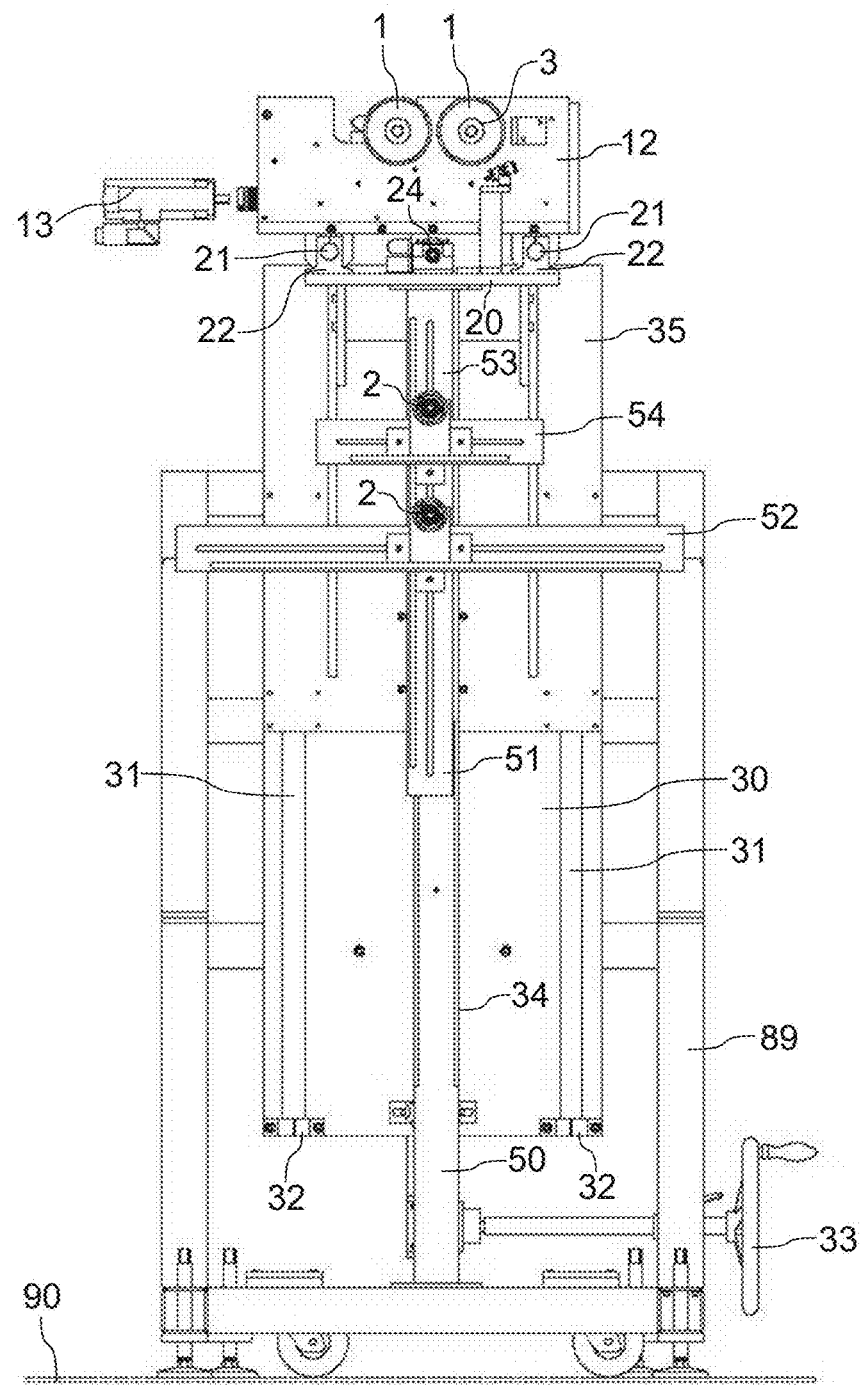
FIG. 2 shows in a front view an apparatus for shaping according to a first embodiment of the present invention.

FIG. 2 shows a front view of an apparatus for shaping according to a first embodiment of the present invention. A base plate 30 is mounted to a machine frame 89 supported on a bottom 90, and a translation stage 35 is mounted to this base plate 30 so as to be vertically displaceable, in order to enable an adjustment of the height of the squeezing rollers 1. This height adjustment can be performed manually using the hand wheel 33, but may also be motorized.

Two guide rods 31 are mounted to the base plate 30, which guide the translation stage 35 vertically. The adjustment is accomplished by means of a threaded spindle 34 which is engaged or coupled, on the one hand, with the hand wheel 33 acting as a vertical adjustment means and, on the other, with the translation stage 35.

According to FIG. 2, the supporting plate 20, on which the squeezing rollers (not shown) are mounted, are connected with the vertical translation stage 35 via a horizontal adapter 38 and a vertical adapter 37. Thus, the height position of the squeezing rollers 1 can be adjusted by adjusting the hand wheel 33. The height position is adjusted such that along the glass tubing strand, which rapidly cools in the direction of drawing, a temperature range is provided in which the glass tubing strand is suitably plastic so that it can be deformed or shaped precisely. This height position can be adjusted once, for example, when starting operation of the plant, or can be adjusted continuously or cyclically by means of the controlling or regulating device 88.

Referring to FIG. 2, the height positions of the deflecting pulleys 2 and their positions transverse to the withdrawal direction of the glass tubing strand can be precisely adjusted or readjusted independently from each other using the height adjustment means 51 and 53 and the transverse adjustment means 52 and 54.

Figure 3:
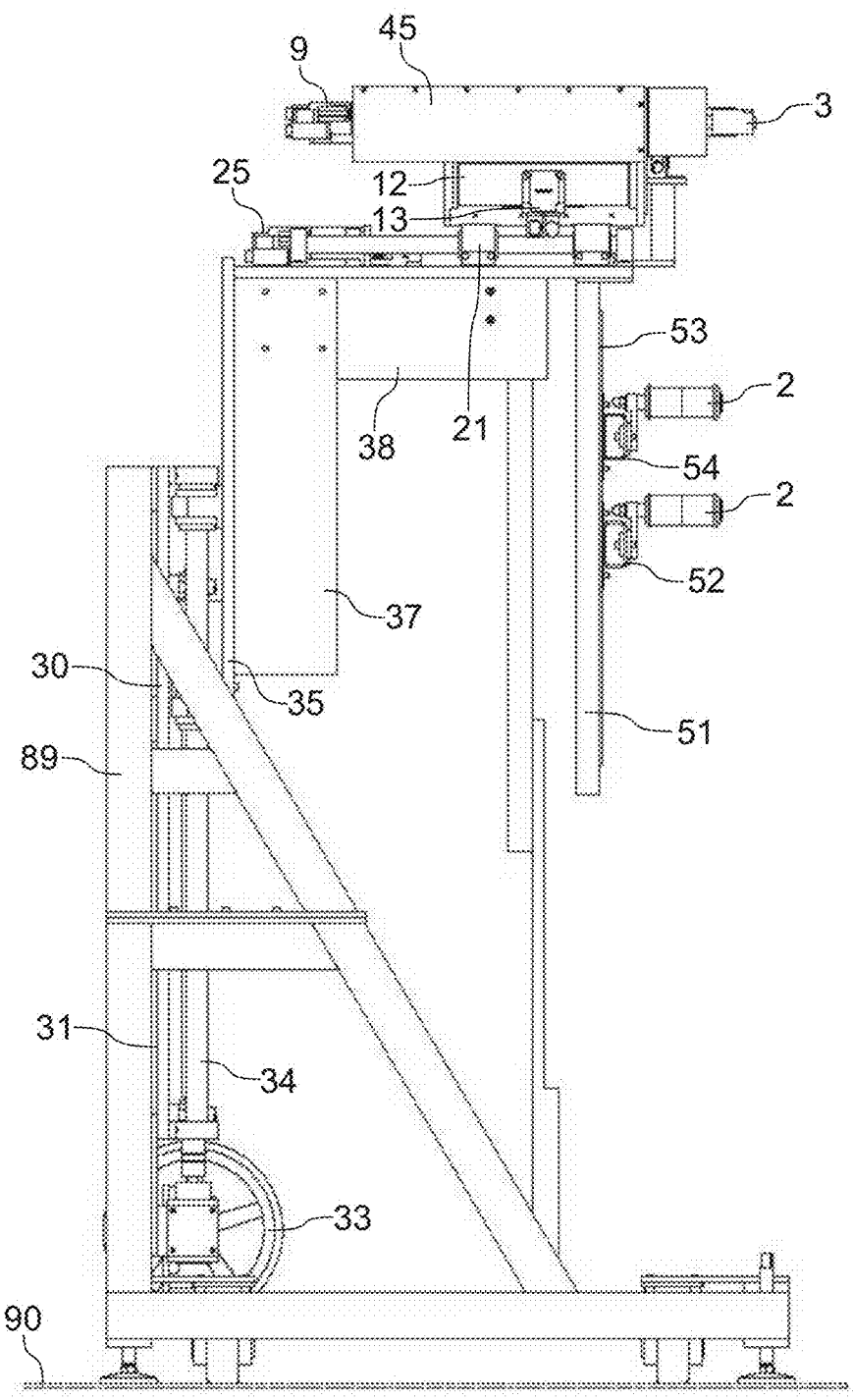
FIG. 3 shows the apparatus of FIG. 2 in a side view.

FIG. 3 shows the apparatus of FIG. 2 in a side view.

Figure 4A:
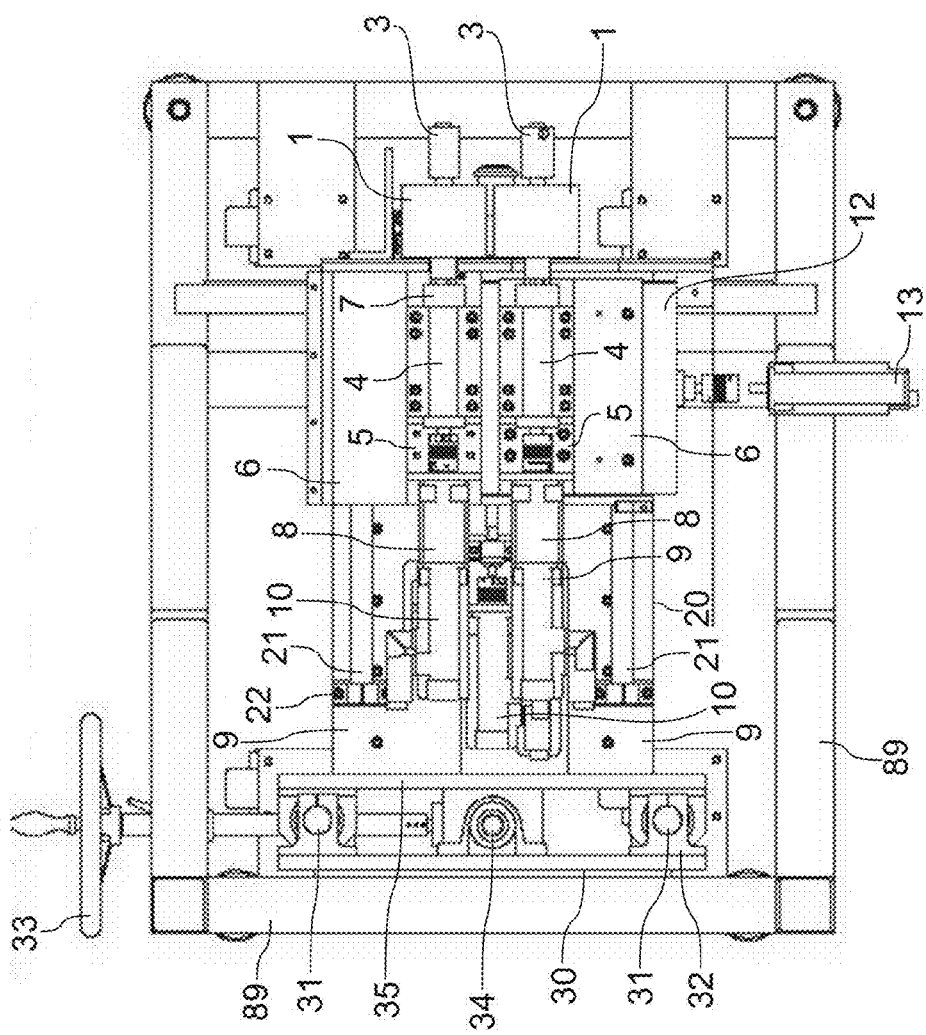
FIG. 4a shows the apparatus of FIG. 2 in a top view without a cover used for shielding the region of shaping.
Figure 6:
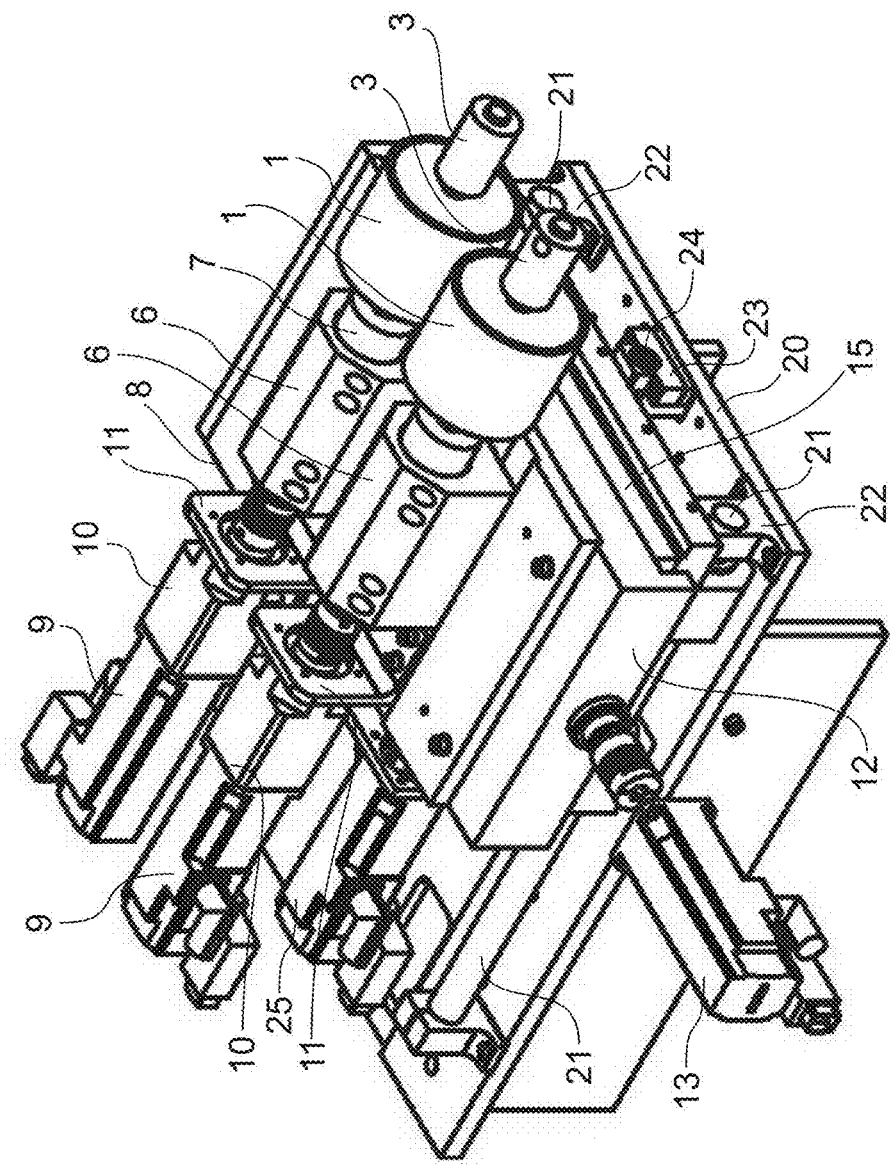
FIG. 6 is a perspective plan view of the upper portion of the apparatus of FIG. 2 with the squeezing rollers.

The further structure used for adjusting the squeezing rollers 1 may be concluded in particular from the top view of FIG. 4a and the perspective view according to FIG. 6. It is noted that the axial adjustment of the squeezing rollers 1 while deforming the glass tubing strand, which will be described in detail in the following, is not essential and that the deforming process generally is also possible if the squeezing rollers 1 are axially fixed. However, the axial adjustment of the squeezing rollers 1 while deforming the glass tubing strand is of advantage for the deforming at high temperatures, particularly for the deforming of glass tubings at high temperatures above the softening point.

As shown in FIGS. 4a and 6, the two squeezing rollers 1 forming a nip are mounted on a translation stage 12 which supports the two squeezing rollers 1. The translation stage 12 can be adjusted in axial direction of the squeezing rollers 1 by means of the adjusting motor 25 for adjusting (displacing) both squeezing rollers 1 together in axial direction.

According to a further embodiment (not shown), the two squeezing rollers 1 forming a nip can be supported on a two-part translation stage 12, one part of which supports one of the two squeezing rollers 1 and the other part of which supports the other of the two squeezing rollers 1. While according to this embodiment a first part of the translation stage 12 is held stationary during the shaping process, the other part of the translation stage 12 may be adjusted in the axial direction of the squeezing rollers 1 relative to the first part of the translation stage 12 by means of the adjusting motor 25.

For guiding the translation stage 12, two mutually parallel guide rods 21 are mounted on the base plate 20 in respective bearing blocks 22. Slide members (not shown) provided on the underside of the translation stage 12, which engage the guide rods 21, guide the axial displacement of the translation stage 12. For adjusting the translation stage 12 a threaded adjustment spindle 24 is further supported on the supporting plate, which is rotationally driven by the servomotor 25 and engages in a counter-thread (not shown) on the underside of the translation stage 12.

The adjusting motor 25 is designed as a synchronous motor, but may also be designed as a stepping motor to allow a step-wise axial displacement, as described in more detail below.

Referring to FIG. 6 further a transverse guide rail 15 is provided on the translation stage 12, which guides the adjustment of the translation stage 12 (or according to the above alternative embodiment of the first part relative to the second part of the translation stage 12) during the adjustment of the width of the nip. For adjusting the width of the nip a servomotor 13 is provided, which is mounted to the supporting plate 20. Thereby, the adjustable squeezing roller 1 can be adjusted relative to the other squeezing roller 1, which is held stationary.

It should be noted that in principle also both squeezing rollers 1 can be adjusted axially.

For driving the rotational movement of the squeezing rollers 1, two servomotors 9 are provided, which are coupled to the associated squeezing roller 1 via a respective gear unit 10 and a respective clutch 8. The clutch 8 is accommodated in a clutch housing having a front end 11, which is formed flange-like and through which tire clutch 8 extends. The clutch 8 couples with the spindle shaft 4, which is supported by means of bearings 5/spindle bearings 7 in a respective bearing block 6 formed as a housing. The squeezing rollers 1 may be mounted to mounting flanges at the front end of the respective spindle shaft 4.

A respective rotary lead-through 3 engages in the front end of the squeezing rollers 1, which may be cooled with air or a fluid, such as water, in order to further cool down the squeezing rollers 1. It should be noted, however, that due to the axial displacement of the squeezing rollers 1, which according to the present invention is carried out continuously during the shaping of the glass tube, such a cooling is not absolutely necessary and may be omitted.

It is possible to control the rotational speed of both squeezing rollers 1 separately. Furthermore, this rotational speed is detected digitally very accurately and is indicated very accurately. This is advantageous for adjusting the shape of the oval tube.

It is possible to synchronize the rotational speeds of the squeezing rollers 1 with the speed of the drawing machine 82 (FIG. 1) at the glass strand or to couple the rotational speeds of the squeezing rollers 1 with a fixed offset. I.e. one may vary the speed of drawing the glass strand and as a result the speed of the squeezing rollers is varied automatically as well.

Figure 4B:
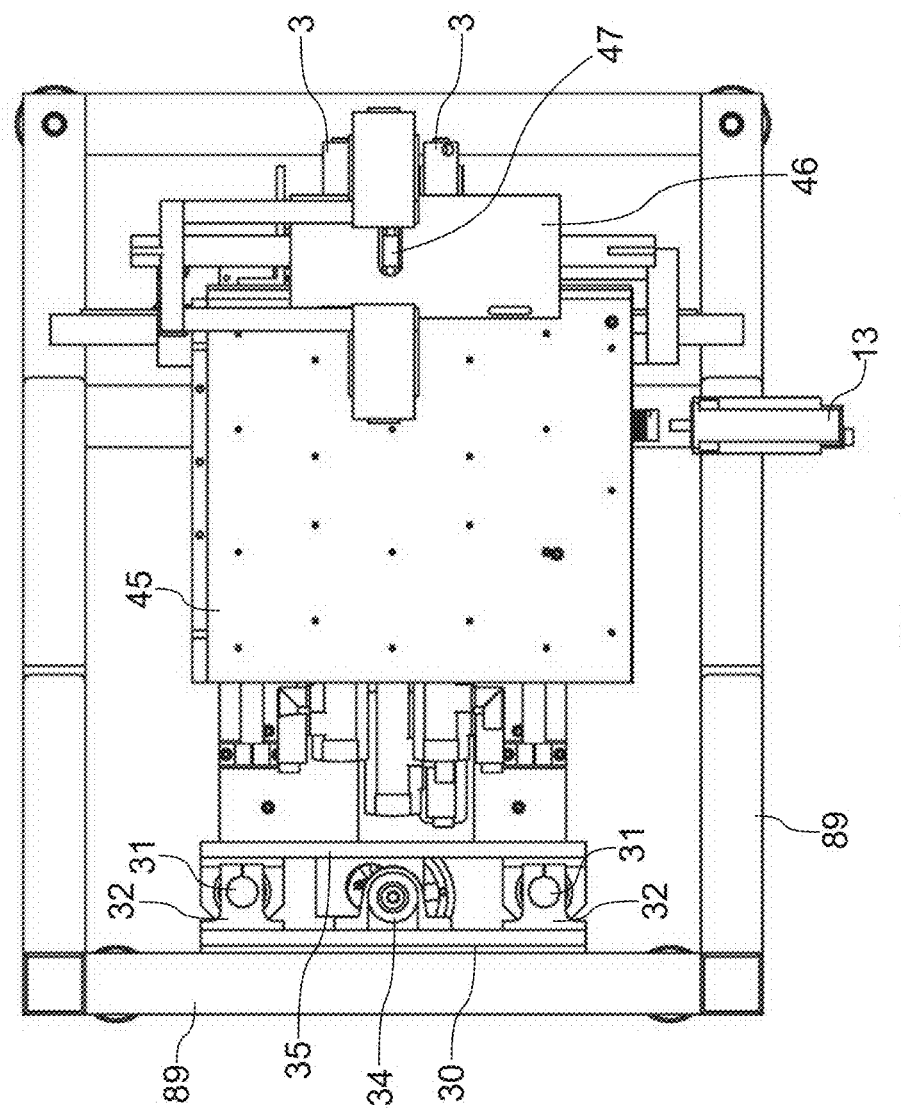
FIG. 4b shows the apparatus of FIG. 2 in a plan view together with the cover used for shielding the region of shaping.

As can be seen in FIG. 4b, in operation the squeezing rollers are jointly accommodated in a housing 45 and covered by a further cover 46, in which an opening 47 is formed, through which the glass tubing strand enters the nip from above for the shaping process.

During the shaping of the glass tubing strand in the nip the position(s) preferably of both squeezing rollers 1 is(are) jointly varied by continuously axially adjusting the positions of the squeezing rollers so that a contact area between the respective squeezing roller and the hot glass body is varied or changed continuously. Preferably this continuous axial adjustment of the positions of the squeezing rollers is performed in accordance with a predetermined only function. This predetermined adjustment function is preferably a cyclic reciprocating movement of the respective squeezing roller 1 in the axial direction thereof corresponding to a sawtooth function or a sinusoidal function or any similar adjustment function, which is preferably performed continuously in time. This will be performed in discrete steps of the same step size.

The precise structure of the system as outlined above enables the adjustment of the movable squeezing roller relative to the stationary squeezing roller at micrometer accuracy. Flaws in the region of the nip can be reduced, on the one hand, by means of the covers 46 and 47 and can be minimized, on the other hand, by means of the controlling or regulating device 88, as described above with reference to FIG. 1. In particular, the effects of temperature in the region of the nip can be detected by a pyrometer, and the shaping (deformation) process may be regulated either manually or automatically. Due to the above configuration of the system, the manipulation of the internal diameter of a squeezed tube at micrometer accuracy is possible with an unprecedented accuracy (for example, an accuracy of ±20 microns has been measured according to the invention). The positions of the squeezing rollers can be controlled in micro degrees, so that the respectively smallest error of the nip width of both squeezing rollers can be determined. The rotation axes of the squeezing rollers, which are driven in synchronism, may be operated at a differential speed using control technology, in order to prevent curvature effects caused by the deflection of the glass strand. The drawing speed (speed of withdrawal of tire glass tube strand or glass rod strand) is determined by the drawing machine, the rollers can be operated at a speed differing therefrom in order to either generate a sag on the glass strand or to exert a pulling effect, which has a significant effect on the geometry of the squeezed glass tube. The controlling and regulating circuit of the system is formed by an optical measurement system, which measures the internal diameter of the squeezed tube with micrometer accuracy, and by the precision servomotors of the respective axes (axes of rotation of the roils, adjustment axes). Furthermore, the pair of squeezing rollers is adjusted stepwise by means of a further servomotor to minimize the amount of wear of the squeezing rollers ahead of schedule due to the strong influence of temperature of the still plastic glass.

The plant and especially the squeezing rollers can be cooled by air or water to minimize the effects of temperature given by the on site conditions.

Figure 5A:
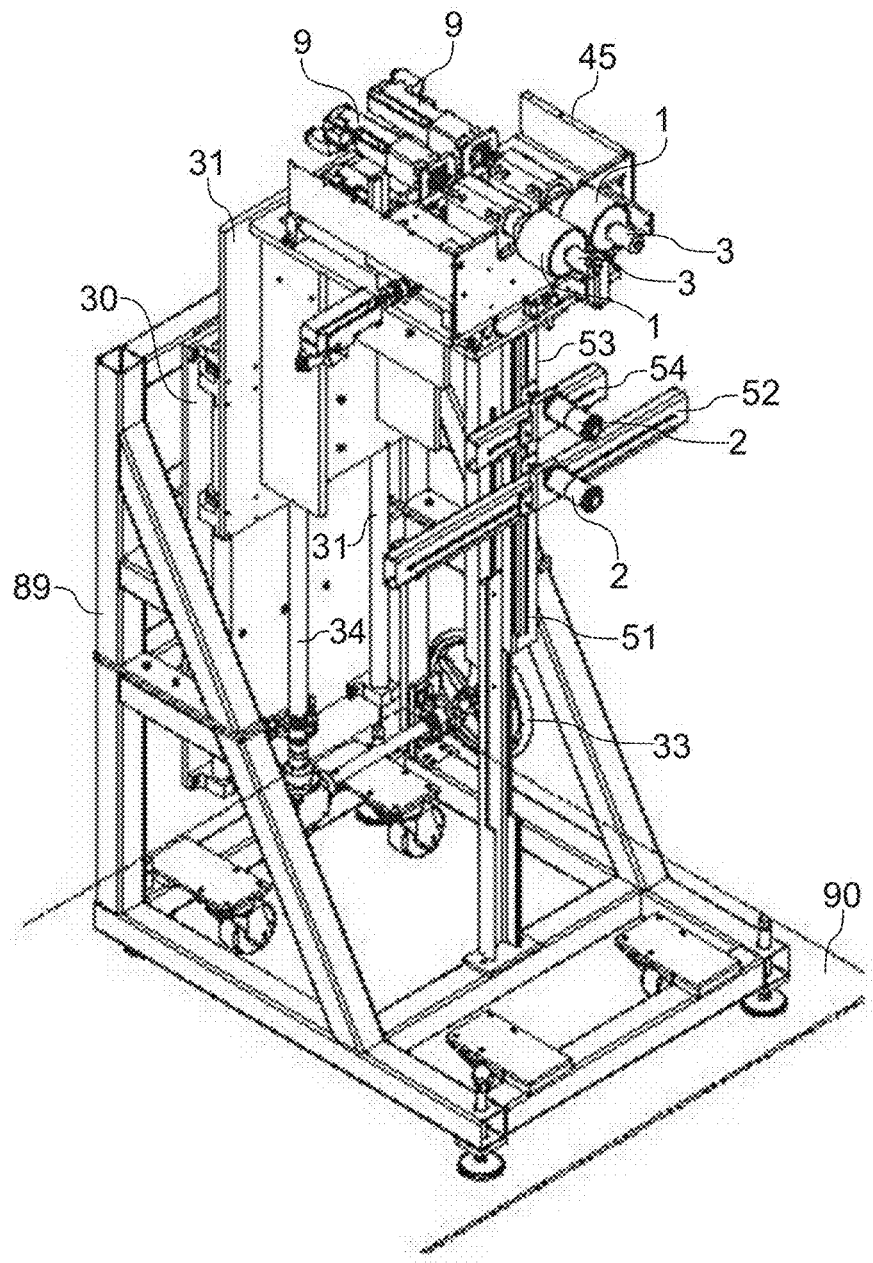
FIG. 5a is a perspective front view of an apparatus for shaping according to a second embodiment of the present invention without a cover used for shielding the region of shaping.
Figure 5B:
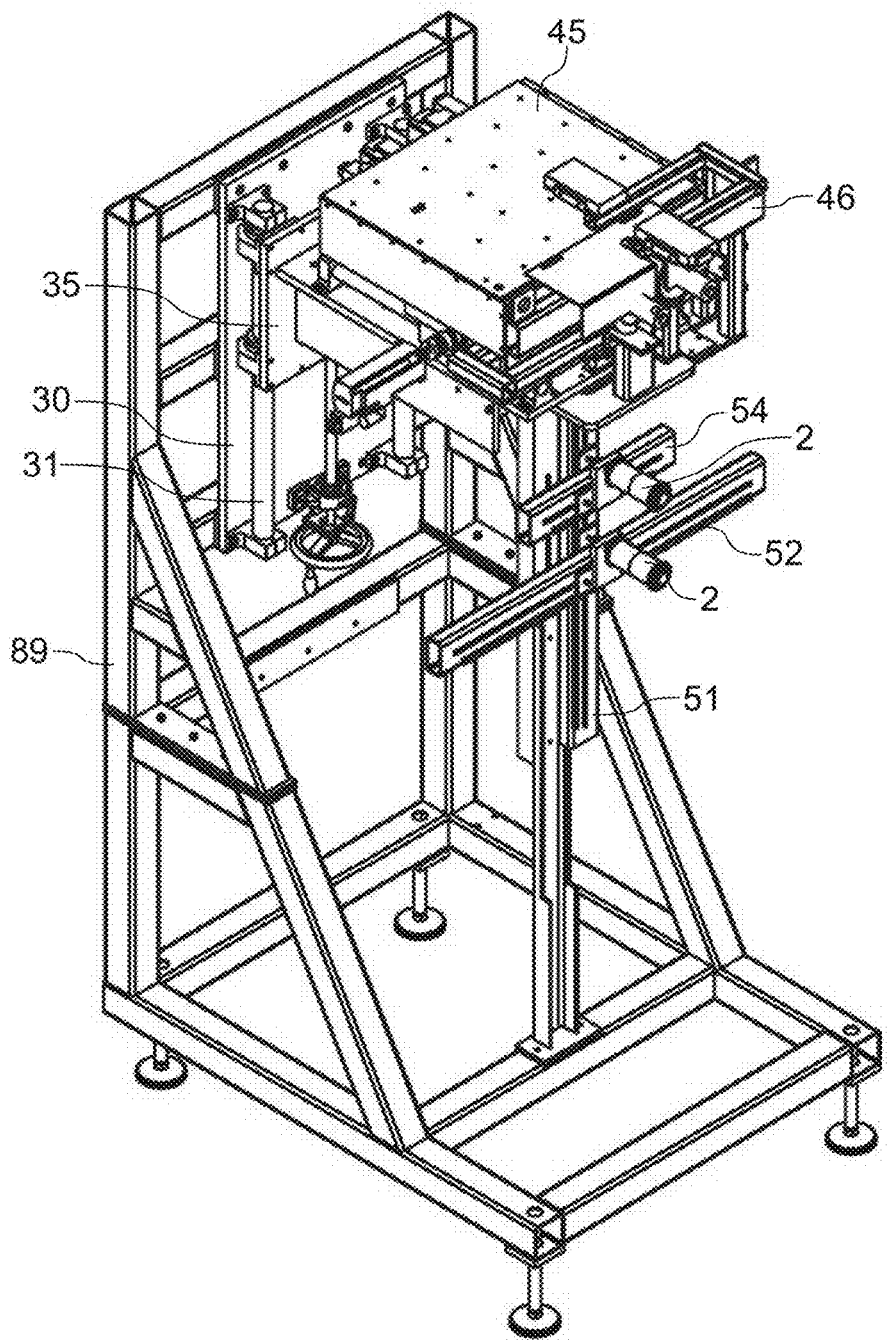
FIG. 5b is a perspective front view of the apparatus of FIG. 5a together with the cover used for shielding the region of shaping.

FIGS. 5a and 5b show two further perspective views of an apparatus for shaping according to the present invention.

FIGS. 7a to 7e show various examples of glass tubes having a non-circular cross-section, which can be produced with high accuracy according to the present invention.

Referring to FIG. 7a, an oval glass tube 100 is formed, having a height H which is less than the maximum transverse dimension L. The bore in the direction of the minor axis is denoted by h. The wall thickness of such an oval tube may be constant over the entire circumference, or may vary continuously and symmetrically, as shown in FIG. 7a. Such an oval glass tube can be used for example as a pre-filler for LED flat screens. A 30% higher light yield was observed. According to a further preferred use according to the present invention such an oval tube can also be used as a tube for conducting a medium flow for photo-bioreactors for illuminating phototropic micro-organisms, which are accommodated in the tube, or for solar-thermal plants for heating a fluid, which flows through the tube, by sun-light, as outlined in the following.

Referring to FIG. 7b, the deformed glass tube 100 is substantially rectangular, having semi-circularly rounded side edges and two longitudinal sides 101 of constant wall thickness extending in parallel with each other.

Referring to FIG. 7c, the glass tube 100 has a longitudinal side 102 and a mirror-symmetrical and convexely curved surface 103, the bending radii in the two corner regions 104 being very small.

According to FIG. 7d, the deformed glass tube 100 overall is dumbbell-shaped and comprises two symmetrically formed oval side wings 105 of a height M2 that are connected with each other via a connecting web 107 of a height M3, which has a smaller width. The inventors have observed that such a glass tube is formed under standard process conditions used for forming an oval tube, as described above with reference to FIG. 7a, if the central side wall portions on the broader side of the glass tube dip a little after the deforming process while being in the hot, malleable state. Here, these central side wall portions can dip a little bit more than shown in FIG. 7d, wherein the side wall portions do not get in contact with each other so that the dumbbell-shaped tube profile has a relatively high mechanical stability.

In the sense of the present invention such glass tubes, as described above with reference to FIGS. 7a to 7d, comprise end portions having a circular profile (cross section), as described hereinafter with reference to FIGS. 7e and 8.

Figure 7E:
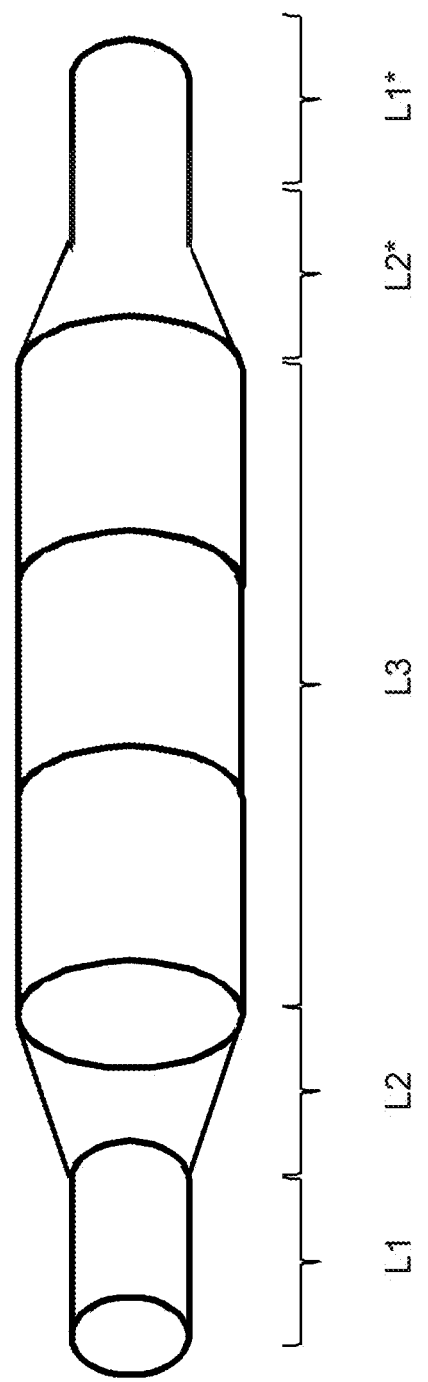

FIG. 7e shows the general configuration of a glass tube according to the present invention. This comprises a central section L3 having a non-circular profile, i.e. a cross section that deviates from a perfect circle. This central section L3 is formed e.g. as an oval tube, as described above with reference to FIG. 7a. Furthermore, the glass tube comprises two open end portions L1 and L1*, i.e. end portions that are not molten off or sealed, which have a circular profile (cross section), which preferably corresponds to the circular profile of the glass tubing strand conveyed into the nip between the squeezing rollers, because the glass tubing strand is not deformed at the end portions L1 and L1*. The end portions L1 and L1* continuously turn into transition portions L2 and L2* and then into the central section L3 having the non-circular profile.

The central section L3 is formed by deforming the glass tube that is conveyed into the nip between the squeezing rollers. In this central section, the width L3 of the broad side of the glass tube corresponds to the distance between the squeezing rollers forming the nip. The end portions of L1 and L1* are preferably not deformed. Rather their circular profiles correspond to the initial profile of the glass tube that is conveyed into the nip between the squeezing rollers prior to the deformation of the central section L3, because during the deforming process of these end portions L1 and L1* the width of the nip is larger than or equal to the outer dimension of the initial profile entering into the nip. The beginning of the transition portions L2, L2* to the end portions L1, L1* indicates that nip width of the nip between the squeezing rollers, which corresponds to the outer dimension of the initial profile that is conveyed into the nip. On further decreasing the nip between the squeezing rollers, the initial profile is increasingly deformed which results in a steady shape of the transition portions L2, L2*. The end of the transition portions L2, L2* to the central section L3 indicates that nip width of the nip between the squeezing rollers that corresponds to a maximum degree of deformation of the initial profile entering into the nip and hence to a minimum outer dimension of the deformed glass tube. For example, this nip width results in a height h of the broad side of the oval tube 100 according to FIG. 7a. For the tube of FIG. 7e the circumferential length of the central section L3, i.e. of the non-circular profile, and the circumferential lengths of the end portions L1, L1* of the tube having the circular profile are equal.

The profiles of the sections L2, L3, and L1* can thereby be suitably set by setting the shape of the squeezing rollers as well as their operation and can be varied in a simple manner. For example, the central section L3 cart be formed so that it is overall drop-shaped, if the axes of the squeezing rollers that form the nip, are adjusted such that they converge in a V-shaped manner while deforming the central section. Or the profile of the central section L3 can vary, if viewed in the axial direction, if the squeezing rollers that form the nip have a non-circular profile, particularly an oval or polygonal profile. Or the central section L3 may have a profile as exemplified in FIG. 7d, if the squeezing rollers that farm the nip have a rotationally symmetric profile deviating from the line-shape contour, particularly if the squeezing rollers together form a mirror-symmetrical nip and if the contour of the respective squeezing roller has a recess and two projections laterally thereto and symmetrically. Of course, more complicated profiles with more than one bulge can be formed in the central section of the tube, if the squeezing rollers that form the nip have two or more than two recesses.

The squeezing rollers may be driven actively and/or be additionally heated. Further, the squeezing rollers can be displaced axially and/or their angle of incidence can be varied.

Figure 8:
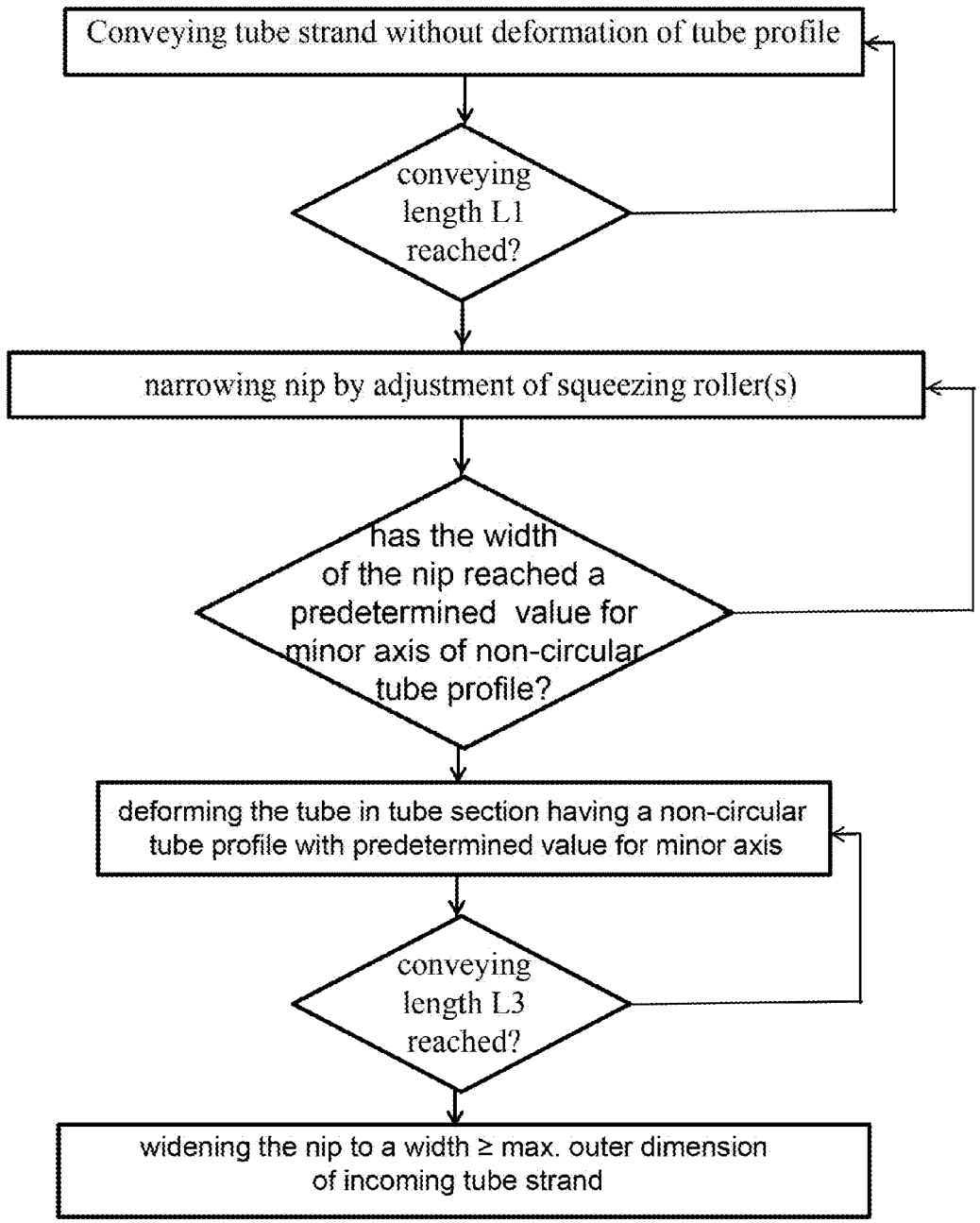
FIG. 8 shows an exemplary flow diagram of a method according to the present invention for the production of a tube having, in sections, a non-circular profile and end portions having a circular profile.

FIG. 8 shows a schematic flow diagram of a method according to the present invention for the production of the glass tube shown in FIG. 7e. At first, a tube having a circular initial profile is provided. For this purpose, the material can be continuously produced by means of a suitable production process, for example by extruding a plastic material, preferably a transparent plastic material, or by continuously drawing a glass tubing strand from a glass melt, for example by means of a down-draw method, a Vello-method or the so-called Danner method. The tube is then conveyed in a malleable (plastically deformable) state through a nip which is formed by at least two squeezing rollers. Depending on the material of the tube a certain heating of the tube may be required for this purpose. Or the tube is further conveyed to the nip directly after its production, for example, by drawing a glass tubing strand from a glass melt or by extruding a plastic tube. In this state, the nip has a first nip width, which is larger than or equal to an outer dimension of the initial profile of the tube, namely the outer diameter of the tube strand entering into the nip. In this operating state preferably no deformation of the tube is performed in the nip, because the squeezing rollers are not in contact with the outer circumference of the tube strand.

After severing a tube previously produced the length of the tube conveyed into the nip (i.e. the conveying length) is measured, for example by means of the length measuring device 91 (see FIG. 1). As long as the measured, tube length does not exceed a predetermined value L1, the squeezing rollers will remain in their idle state and the tube is not deformed in the nip. If the measured tube length has reached the predetermined value L1, it is started to reduce the width of the hip by adjusting at least one squeezing roller in a direction perpendicular to the axial direction thereof. The time of direct contact of the squeezing rollers on the outer circumference of the tubing strand entering into the nip indicates the beginning of the transition portion L2. By further reducing the width of the nip, the tube is progressively deformed and finally the width of the nip reaches a predetermined value (the second nip width), which corresponds, for example, to the minor axis of the oval tube to be produced. This time indicates the end of the transition portion L2 and the beginning of the central section L3 of the glass tube having the non-circular profile.

After reaching the second nip width, which is smaller than the outer dimension of the initial profile of the tubing strand entering into the nip, the tube is deformed in the malleable state to the non-circular profile L3, i.e. to a profile deviating from the circular shape. Here, the deformation to an oval tube is conceived, as exemplified in FIG. 7a, but also to any other profiles that are different from the ideal circular shape and have been described above in an exemplary manner and with reference to FIGS. 7b to 7d. In this operating state, the conveying tube length is still measured. As long as the measured, conveying length of the tube has not exceeded a predetermined value L3, the squeezing rollers will remain in the state with the second nip width, in which the tube is deformed in the nip. If the measured conveying length of the tube has reached the predetermined value L3, it is started to increase again the width of the nip by adjusting at least one squeezing roller in a direction perpendicular to the axial direction thereof. The time of starting with this increase of the nip indicates the beginning of the rear transition region L2*. By further increasing the width of the nip, the tube is deformed by an increasingly smaller extent until, finally, the width of the nip again is larger than or equal to the outer dimension of the initial profile (third gap width, which may be equal to the second gap width). This time indicates the end of the rear transitional portion L2* and the beginning of the rear end portion L1*, where the tube again has a circular profile corresponding in particular to the profile of tire initial profile that has not been deformed and runs into the nip. Finally, the tube is severed at an appropriate location in the rear end portion L1*.

As will become apparent to the person skilled in the art, in this manner tubes can be produced, whose end portions L1, L1* are circular, so that these end portions L1, L1* can be connected with connecting members (e.g. inlet and outlet) or with adjacent lubes using conventional tube connecting technologies, which, however, have at least one central section L3 having a suitable profile deviating from the circular shape. In this manner according to the present invention tubes partially having a non-circular profile can still be connected with tube connecting members or adjacent tubes using proven tube connecting technologies. With the method according to the present invention, as described above with reference to FIG. 8 by way of example, any profile curves can also be adjusted in the axial direction of the tube. In general, symmetrical profile curves are preferred, as shown in FIG. 7e, because these can be produced with less strain. In general, however, it is conceived to produce any other profile curves that are asymmetric in axial direction.

Fields of application of such tubes, particularly of such glass tubes, are for example: oval tubes with high geometric accuracy for the use for the hermetic packaging of nanoparticles of semiconductor material, wherein a high geometric accuracy (bore) is important; piston tubes or sheath tubes for discharge lamps, particularly flash lamps, where the fitting dimension should be minimized but not the light yield.

Figure 10B:
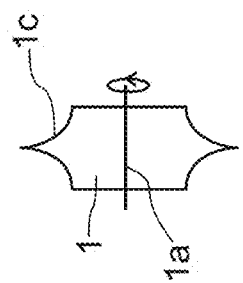
Figure 10A:
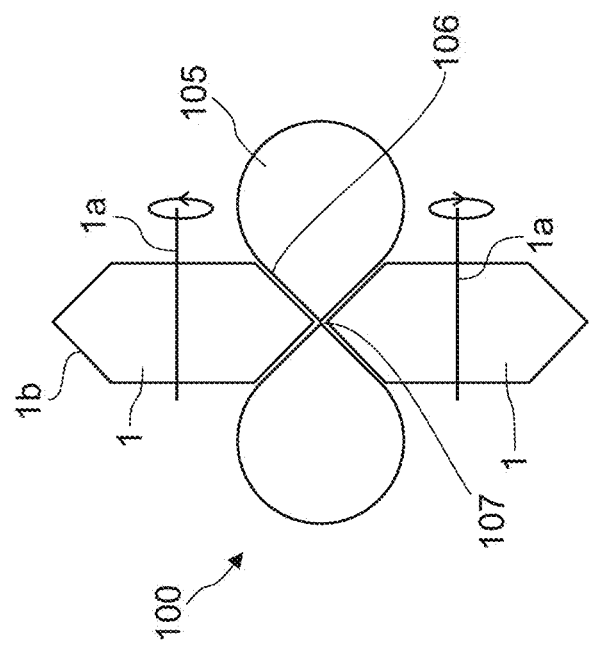
FIG. 10a shows the region of a nip that is formed by two squeezing rollers for a method according to a further embodiment of the present invention.

Referring to FIGS. 10a and 10b, in the following a method according to a further embodiment of the present invention will be described. In FIG. 10a the region of the nip, which is formed by two squeezing rollers 1, is shown in a schematic sectional view. The glass tube 100 passes through the nip perpendicular to the plane of the drawing. The squeezing rollers 1 rotate about the respective axis 1a. Deviating from the embodiment shown in FIGS. 2 to 6, the squeezing rollers 1 have a projection 1b on their outer circumference, which has the shape of an isosceles triangle in the illustrated embodiment, whereas the present invention generally shall not be limited to this profile. In the position according to FIG. 10a the squeezing rollers 1 form a nip, which widens symmetrically and in a wedge-shaped manner starting from the narrowest point, namely where the apexes of the projections 1b are opposite to each other. The glass tube 100 is deformed by the nip to such an extent that a constriction 107 is formed in the central section, where the top and bottom side of the glass tube contact each other and fuse together to form a connecting web 107. Starting with the connecting web 107 slanted connecting legs 106 extend outward, wherein the shape and inclination is determined by the profile of the projections 1b of the squeezing rollers 1 and wherein the connecting legs 106 finally merge into two spherical side wings 105. A glass tube 100 of such a shape thus defines two flow channels that are formed by the side wings 105. In the region of the connecting web 107 these flow channels are separated from each other, so that for example in this region fluids can flow in opposite directions.

FIG. 10b shows a further embodiment of a squeezing roller 1, which has a projection 1c with a concave curvature. This results according to FIG. 10a in a corresponding convex curvature of the glass tube (not shown) in the region, of the connecting leg.

Figure 9C:
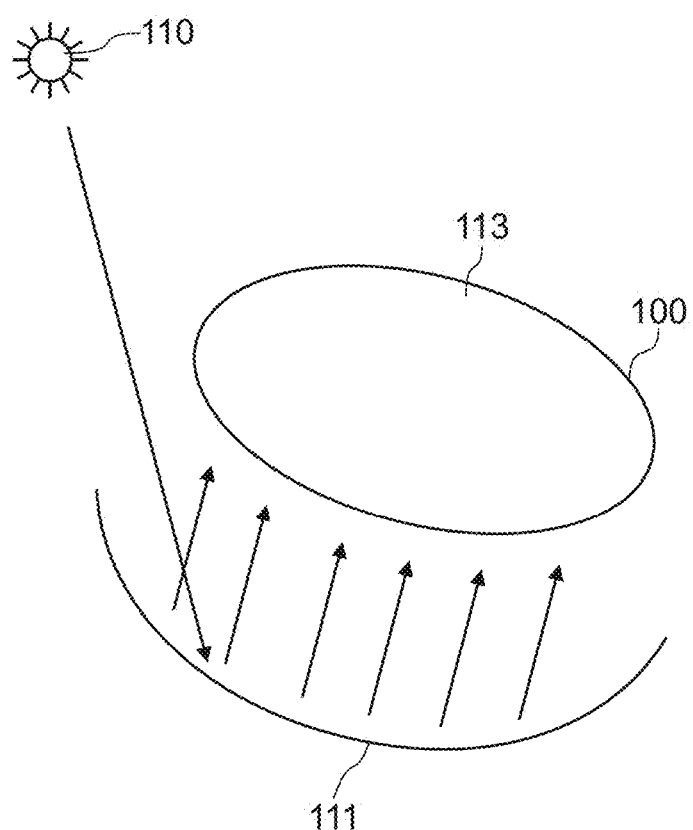
FIG. 9c shows the use of a tube according to the present invention for solar heating.

Referring to FIGS. 9a to 9c, two preferred applications of a glass tube according to the present invention will be described in the following. FIG. 9a shows the use of a transparent tube according to the present invention in a photobioreactor for cultivating phototropic organisms or microorganisms, in particular of (micro) algae, by irradiation, with natural light. In the transparent tube 100, which may be formed of glass or a suitable transparent plastic material, a liquid 113 is accommodated which contains the microorganisms 112 to be grown as a matrix, such as algae. The tube 100 is connected with connecting members, i.e. an inlet and an outlet (not shown), or with additional tubes of the same kind, if necessary via intermediate members or coupling members, via its end portions having the circular profile, so that the liquid 113 with the microorganisms 112 may be pumped through the photobioreactor continuously or in a pulsed manner. The tube 100 has at least one central section having a non-circular profile, and is otherwise shaped as described above with reference to FIG. 7e. This central section is formed for example as the oval tube illustrated. When used according to the present invention, the broader part of the central section (L3) of the tube 100, e.g. the illustrated oval tube, is disposed facing the natural light source (sun) 110. More specifically, the major axis, which runs through the two focal points of the oval tube 100, is perpendicular to the direction of incidence of the light or to an average direction of incidence of light, which is averaged over a normal course of irradiation of the light.

As will become apparent to the person skilled in the art, in the arrangement of FIG. 9a the natural light source can also be imaged, in a suitable manner onto the tube 100 by means of concave mirrors or similar optical imaging devices, wherein then the arrows shown in FIG. 9a shall represent the direction of incidence of the sun light. In such a case, e.g. the central section (L3) of the oval tube shown would be disposed in a similar manner with the wider part facing the sunlight or the direction of incidence of the sun light. Particularly in the case that the solar radiation is incident on the tube 100 without optical imaging means, the tube 100 is generally not exactly (in the mathematical sense) disposed lacing with its wider side the direction of incidence of the sun light, but only approximately, because the tube 100 is generally not adjusted in accordance with the changing position of the sun. Of course, such an adjustment of the orientation of the tubes 100 of the photobioreactor could in principle also be provided to allow for optimum solar radiation absorption in the tube 100 of the present invention. As an alternative, the imaging of the sun light onto the tube 100 is adjusted by a suitable adjustment of the concave mirror or of similar optical imaging devices in accordance with the position of the sun.

FIG. 9b shows the use of a transparent tube 100 according to the present invention in a photobioreactor for cultivating phototropic organisms, in particular microorganisms, by irradiation with artificial light. According to FIG. 9b the artificial light source 115 is placed at the focus of a concave mirror 111, extending along the respective central section and parallel to the latter, so that the light of the artificial light source 110 is imaged in an expanded, light beam, which irradiates the tube 100. Here, the central section (L3) of the tube 100, e.g. of the illustrated oval tube, is disposed such that its broader side faces the light source 115. More specifically, the major axis which runs through the two focal points of the oval tube 100, are oriented perpendicular to the direction of light incidence, which is defined by the concave mirror 111 and the position of the light source 115.

Numerical example: As compared to a round tube an oval tube (with the same circumference) and a major axis ratio of e.g. 1.42:1 has a surface area which is larger by a factor of 1.16. But because of die slightly smaller cross-section, the algae flow faster in the oval section than in the circular section and are exposed for a shorter period of time (shorter by a factor of 1.06). Taken together, the present invention, however, offers a positive effect by a factor of 1.09. This factor corresponds to an enhanced algal growth as compared to a fully round tube. Thus, algae can be grown in photobioreactors in tubes, wherein a plurality of tubes are connected to quasi-endless tubes (for example, up to 50 m in length) that can be disposed vertically one above the other and with stands to be exposed to the sun or an artificial light source. According to the present invention the combination of oval tubes with circular end portions is advantageous to take advantage of the enhanced luminous efficiency, and the conventional connecting techniques of circular tubes.

FIG. 9c shows a further use of a tube 100 in accordance with the present invention for use in the solar heating for heating a fluid by means of sunlight. In the transparent tube 100, which may be formed of glass or a suitable plastic material, a liquid 113 is accommodated, which is to be heated. The tube 100 is connected with connecting members, i.e. an inlet and an outlet (not shown), or with additional tubes of the same kind, if necessary via intermediate or coupling members, via its end portions having the circular profile, so that the liquid 133 can be pumped through the solar thermal system continuously or in cycles. The tube has at least one central section having a non-circular profile, and is otherwise shaped as described above with reference to FIG. 7e. This central section is formed for example as the illustrated oval tube 100. When used according to the present, invention the central section (L3) of the tube, e.g. of the illustrated oval tube, is disposed facing with its wider side a light source. According to FIG. 9c the light from the sun 110 is imaged by a concave mirror 111 onto the tube 100, which extends along the respective central section and parallel to the latter, so that the sunlight of the light source is imaged to a widened light beam, which irradiates the tube 100. In this geometry, the wider side of the tube 100 is disposed facing the concave mirror 111, which serves here as a light source for heating the fluid 113 in the tube 100. Usually, the concave mirror 111 is adjusted according to the varying position of the sun. In simpler, less efficient solar systems, however, this need not necessarily be the case, in which case the orientation of the tube described above is not necessarily exact (in the mathematical sense), but rather an approximation to an optimum orientation approximated as best as possible. Because of the oval tube sections tolerances in the geometry of the mirrors and in the sun tracking system may be generally larger and thus costs can be saved.

As materials for the tube according to the present invention, any deformable material may be used, for example, glass, plastic material or plastic composite materials. For the preferred applications according to the present invention, in which a fluid accommodated in the tube is to be irradiated, the material of the tube is suitably transparent in the wavelength range of the irradiating light. Preferably, for this purpose transparent glass types, such as Duran ($SiO_2$-81%, $B_2O_3$-13%, $N_2O+K_2O$-4%, $Al_2O_3$-2%), soda lime glass or Fiolax®, or transparent plastics materials are used selected from a group consisting of: polymethylmethacrylate (PMMA), polycarbonate (PC), polyamide (PA), polyethylene (PE), polypropylene (PP), polystyrene (PS), poly-4-methylpenten-1 (PMP), polyvinylchloride (PVC), cycloolefincopolymers (COC), styrene/butadiene/Styrene-bolckcopolymere (SBS), methylmethacrylate/acrylnitrile/polybutadiene/styrolpfropfcopoylmere (MABS), aromatic polyesters (APE), polyestercarbonate (PEC), cellulose propionate (CP), polyetherfluorethylene (PTFE), polyethersulfone (PES).

The tube length can be 0.20 m-10 m, the diameter in the circular section may be larger than 8 mm and smaller than 200 mm, the wall thickness can be in the range 0.5 to 10 mm. Oval tubes according to the present application may be provided with major axes a and b (longest and shortest diameter, respectively) and with axes ratios 1<a/b<2, and more preferably 1.2<a/b<1.6.

Referring to FIG. 1, the glass tube may be marked in accordance with the outer dimensions and/or internal dimensions detected downstream of the nip by means of the measurement devices 86, 87, for example by means of labeling or laser marking. Furthermore, the glass tube may also be sorted in accordance with the outer dimensions and/or internal dimensions detected downstream of the nip by means of the measurement devices 86, 87.

For an apparatus for squeezing of viscoplastic glass tubing with a tolerance of the inner diameter of +/−20 microns, the requirements with regard to the tolerances of the components are generally at a 10-fold accuracy of the tolerance specifications. To keep the costs at tolerable levels, conventionally the individual components of the apparatus were produced to have tolerances of max.+/−3 microns. The influence of temperature needs to be taken into consideration, because a change in temperature of 1K results in a change of the nip width of 1 micron. Therefore, the temperature of the whole system may be kept as constant as possible optionally by means of a cooling system. However, the surfaces of the squeezing rollers usually are heated uncontrollably by the glass tube strand or glass rod strand, which can be avoided by the continuous axial adjustment of at least one of the squeezing rollers, and preferably of both squeezing rollers, as described above. This can be supported further by the continuous monitoring and controlling or regulation of the width of the nip.

Figure 11A:
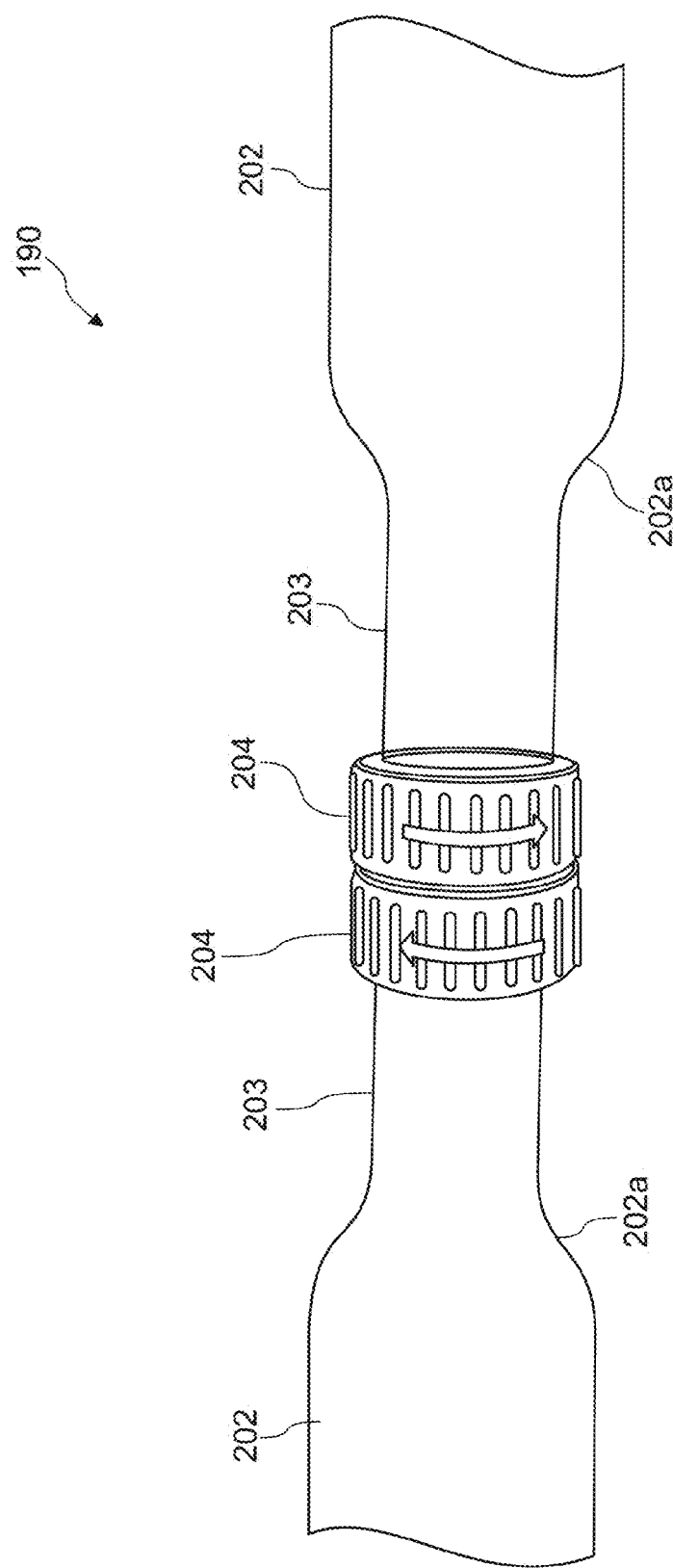
FIG. 11a shows the coupling of two tubes according to the present invention.

FIG. 11a shows an example for a connecting assembly 190 for connecting two tubes according to the present invention. Only the end portions of the tubes 203 having a circular profile are shown, which turn into the respective portions 202 having a non-circular profile via the transition portions 202a in, as described above. The two end portions 203 having a circular profile are each surrounded by a sleeve-shaped tube connector 204. The two tube connectors 204 are preferably connected to each other, but may also be integrally formed. By rotation of the respective tube connector 204, as shown in FIG. 11a by the rotation arrow, a tight connection between the respective tube connector 204 and the respective end portion 203 having a circular profile is accomplished. For example, by rotation of the tube connector an end cap thereof is adjusted in axial direction, whereby an O-ring is compressed, which seals the end portion 203 having a circular profile.

Figure 11B:
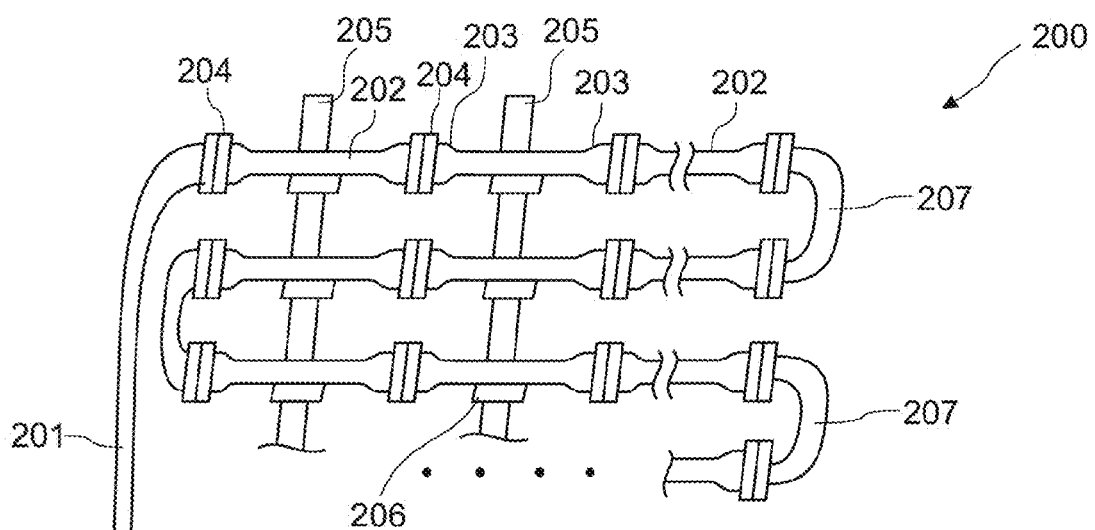
FIG. 11b schematically shows a photobioreactor for cultivating micro-organisms by illumination according to the present invention.

FIG. 11b shows a schematic view of a photobioreactor 200 for cultivating microorganisms by irradiation according to the present invention, for example for cultivating algae. Growing algae use light and certain nutrients, primarily carbon dioxide, soluble nitrogen compounds and phosphate. Sunlight is typically used as light, but artificial light can be used as an alternative to or in addition to natural light. A small amount of microorganisms are admixed to a liquid, for example water, especially fresh water or sea water, or a suitable nutrient fluid. The photobioreactor 200 comprises a plurality of tubes, which are suitable transparent, so that light can penetrate into the liquid, which is accommodated in the tubes. The tubes each comprise portions 202 having a non-circular profile and portions 203 having a circular profile, as described above. The tubes are connected with each other via connecting members 204, which are e.g. configured, as described above with reference to FIG. 11a. A plurality of tubes is connected together in series in this manner to thereby form a respective row. The individual rows are connected with each other by U-tubes 207, so that overall a meandering arrangement of tubes is implemented in which the liquid with the microorganisms is accommodated and flows suitably. The first and last row, respectively, of the tubes can be connected via a connection line 201 to storage tanks, pumps, etc. (not shown). The tubes are supported in a frame 205 by supporting members 206, which allows a proper alignment of the tubes, as described above.

Although it has been described above that the tubes have a section with a circular profile at both ends, it will become apparent to the skilled person that the tubes may be severed to length in a suitable manner also at any other location during or after their production. Conceivable are, for example, tubes which comprise a section having a circular profile to be connected to adjacent tubes as well as at least one other section having a non-circular profile, wherein the tubes are severed to length in the section having the non-circular profile. Such tubes have, for example, an end having a circular profile and an opposite end having a non-circular profile. According to the embodiment of FIG. 10a, the tube can for example be shaped as a dumbbell-shaped double tube, i.e. without any end portion having a circular profile, wherein the connection with the flow channels formed by the side wings 105 is then accomplished in a different manner, for example by means of hoses.

Although it has been described above that the apparatus is used for shaping (deforming) of glass tubes, the apparatus may be used in a corresponding manner also for the shaping (deforming) of tubes made of other durable materials that can be deformed plastically. Preferably, the initial glass tube or initial tube has a circular cross section and the shaping (deforming) is performed to obtain a different profile in at least one central section. The tube ends are open and have a constant profile in the region of the end portions, i.e. they are not molten off or sealed by other measures. As will be readily apparent to the person skilled in the art upon reading the above description, the invention has been described above only by way of example and with reference to exemplary embodiments. Various modifications may be implemented without departing from the general concept and the scope of the present invention as set forth in the appended claims. Further, according to the present invention the features described above may be combined in a different manner as particularly disclosed above.

LIST OF REFERENCE NUMERALS

1 Squeezing rollers
1a rotation axis
1b triangular projection on outer circumference of squeezing roller 1
1c projection on outer circumference of squeezing roller 1 having a concave bulge
2 guide pulleys
3 rotary lead-through
4 spindle shaft
5 bearing
6 bearing block
7 spindle bearing
8 clutch
9 servomotor
10 gear unit
11 flange
12 translation stage
13 adjustment of nip
15 guide rail
20 support plate
21 guide rod
22 bearing block
23 bearing block
24 adjusting spindle (for axial adjustment of rollers)
25 motor (for axial adjustment of rollers)
30 base
31 guide rod
32 bearing block
33 turning wheel (for height adjustment)
34 adjusting spindle
35 translation stage
37 adapter
38 adapter
45 cover with cooling unit
46 cover
47 opening
50 holding web
51 height adjustment
52 transverse adjustment
53 height adjustment
54 transverse adjustment
80 glass tube production line
81 glass tubing strand
82 drawing machine
83 pair of drawing rollers
84 pair of drawing rollers
85 frame
86 measurement device for outer diameter
87 measurement device for inner diameter
88 central control or central regulation
89 frame
90 bottom
91 length measuring device
92 severing device 100 glass tube
101 longitudinal side
102 flat longitudinal side
103 convex curved side
104 corner area
105 side wing
106 slanged leg
107 constriction/connecting web
110 natural light source (sun)
111 concave mirror
112 microorganisms
113 fluid
115 artificial light source
190 tube connecting assembly
200 photobioreactor
201 connecting line
202 section of tube having non-circular profile
202a transition portion
203 section of tube having circular profile
204 tube connector
205 frame
206 support member
207 U-tube

What is claimed is:

1. A method for the production of a tube for conducting a medium flow for photo-bioreactors, the tube having, in sections, a non-circular profile by deforming, comprising:
   a) providing a tube, which has a circular initial profile;
   b) conveying the tube in a hot, malleable state through a nip, which is formed by squeezing rollers and has a first nip width, which is larger than or equal to an outer dimension of the initial profile;
   c) adjusting the squeezing rollers for setting a second nip width, which is smaller than the outer dimension of the initial profile, and deforming the initial profile in said hot, malleable state for obtaining said non-circular cross section; and
   d) adjusting the squeezing rollers for setting a third nip width, which is larger than or equal to the outer dimension of the initial profile, and severing said tube in a region having a circular cross section;
   so that respective end portions of said tube have a circular cross section.

2. The method for the production of a tube according to claim 1, wherein a circumferential length of said non-circular profile and the circumferential length of said end portions of said tube having a circular cross section are equal to each other.

3. The method for the production of a tube according to claim 1, wherein a conveying length of the tube is measured, wherein an axial length of a section having said non-circular cross section and/or an axial length of transition portions between the end portions of the tube and said non-circular profile is/are adjusted on the basis of a value for the respective conveying length.

4. The method for the production of a tube according to claim 3, wherein the adjusting of the squeezing rollers in steps c) and d) is performed according to a predetermined adjustment function for forming the transition portions between the end portions of the tube and said non-circular profile such that these transition portions have cross sections in accordance with the predetermined adjustment function.

5. The method for the production of a tube according to claim 1, wherein the deforming of the initial profile to said non-circular profile in step c) is performed in a hot, malleable state, wherein the position of at least one of the squeezing rollers is continuously varied so that a contact area between the respective squeezing roller and the hot tube running into said nip is continuously varied.

6. The method for the production of a tube according to claim 5, wherein the position of the respective squeezing roller is varied by a continuous axial adjustment of the respective squeezing roller.

7. The method for the production of a tube according to claim 6, wherein the continuous axial adjustment of the respective squeezing roller is performed in accordance with a predetermined adjustment function, wherein the predetermined adjustment function
   is a cyclic reciprocating movement of the respective squeezing roller, which is performed in the axial direction of said respective squeezing roller, and/or
   is performed in discrete steps, each having the same step size.

8. The method for the production of a tube according to claim 1, wherein the squeezing rollers, which form said nip, have a non-circular profile.

9. The method for the production of a tube according to claim 1, wherein the squeezing rollers, which form said nip, have a rotationally symmetric profile and a contour, which deviates from a linear shape.

10. The method for the production of a tube according to claim 9, wherein the squeezing rollers form a mirror-symmetric nip, wherein a contour of the respective squeezing roller comprises at least one recess or at least one projection.

11. The method for the production of a tube according to claim 1, wherein
    the squeezing rollers are driven actively and/or are heated additionally, and/or
    the squeezing rollers are adjusted in axial direction and/or an angle of inclination of said the squeezing rollers is varied.

12. The method for the production of a tube according to claim 1, wherein the tube having the circular initial profile is made of a transparent or non-transparent glass.

13. The method for the production of a tube according to claim 1, wherein the tube having the circular initial profile is made of a transparent or non-transparent plastic material, wherein the plastic material is selected from a group consisting of: polymethylmethacrylate (PMMA), polycarbonate (PC), polyamide (PA), polyethylene (PE) polypropylene (PP), polystyrol (PS), poly-4-methylpentene-1 (PMP), polyvinylchloride (PVC), cycloolefincopolymer (COC), styrol/butadiene/styrol-bolckpolymer (SBS), methylmethacrylate/acrylnitrile/polybutadiene/styrolpfropfcopoylmere (MABS), aromatic polyesters (APE), polyestercarbonate (PEC), cellulose propionate (CP), polyetherfluorethylene (PTFE), polyethersulfone (PES).

14. A method for the production of a tube for conducting a medium flow for photo-bioreactors, the tube having, in sections, a non-circular profile by deforming, comprising:
    a) providing a tube, which has a circular initial profile;
    b) conveying the tube in a hot, malleable state through a nip, which is formed by squeezing rollers and has a first nip width, which is larger than or equal to an outer dimension of the initial profile;
    c) adjusting the squeezing rollers for setting a second nip width, which is smaller than the outer dimension of the initial profile, and deforming the initial profile in said hot, malleable state for obtaining said non-circular cross section; and
    d) adjusting the squeezing rollers for setting a third nip width, which is larger than or equal to the outer dimension of the initial profile, and severing said tube in a region having a circular cross section;

so that respective end portions of said tube have a circular cross section, and wherein the tube has a diameter in the circular section that is greater than 8 millimeters.

* * * * *